(12) United States Patent
Bosch

(10) Patent No.: US 6,519,601 B1
(45) Date of Patent: Feb. 11, 2003

(54) RELATIONAL DATABASE COMPILED/STORED ON A MEMORY STRUCTURE PROVIDING IMPROVED ACCESS THROUGH USE OF REDUNDANT REPRESENTATION OF DATA

(75) Inventor: Bart Van Den Bosch, Houwaartstraat 64, B3210 Linden (BE)

(73) Assignees: Universitaire Ziekenhuizen Leuven, Leuven (BE); Bart Van Den Bosch, Linden (BE)

( * ) Notice: Subject to any disclaimer, the term of this patent is extended or adjusted under 35 U.S.C. 154(b) by 0 days.

(21) Appl. No.: 09/194,557

(22) PCT Filed: May 21, 1997

(86) PCT No.: PCT/BE97/00062

§ 371 (c)(1), (2), (4) Date: Nov. 23, 1998

(87) PCT Pub. No.: WO97/44745

PCT Pub. Date: Nov. 27, 1997

Related U.S. Application Data

(60) Provisional application No. 60/018,140, filed on May 22, 1996.

(30) Foreign Application Priority Data

May 22, 1996 (EP) .............................. 96870066

(51) Int. Cl.⁷ .............................................. G06F 17/30
(52) U.S. Cl. ......................... 707/100; 707/102; 707/2; 707/3; 707/203; 705/2
(58) Field of Search ................................. 707/3, 2, 100, 707/203, 102; 705/2

(56) References Cited

U.S. PATENT DOCUMENTS

| | | | | |
|---|---|---|---|---|
| 5,361,202 A | * | 11/1994 | Doue | 705/3 |
| 5,942,986 A | * | 8/1999 | Shabot et al. | 340/825.44 |
| 5,950,210 A | * | 9/1999 | Nelson | 707/203 |

FOREIGN PATENT DOCUMENTS

| | | |
|---|---|---|
| EP | 320 266 A | 6/1989 |
| GB | 2 172 130 A | 9/1986 |

* cited by examiner

Primary Examiner—Jean R. Homere
(74) Attorney, Agent, or Firm—Knobbe, Martens, Olson & Bear, LLP

(57) ABSTRACT

A relational database compiled/stored on a computer environment for storing data about units of work includes a first set of tables and a second set of tables. The first set of tables includes first columns and first tuples and a first dataset containing first data included in the first columns and first tuples. The second set of tables includes second columns and second tuples and a second dataset consisting of second data. The data included in the second columns and second tuples being second data. The units of work including first services, final services and current services. The unit of work having a status being inactive, active or terminated. The second data is a redundant representation of a part of the first data.

40 Claims, 23 Drawing Sheets

```
CREATE TABLE X#FOO (
    dkey                            null,
    omit            omitchar        not null,
    sender          sender_name     not null,
    sendTime        sendTime        not null,
    omitter         omitterName     null,
    omitTime        omitTime        null,
    cdkey           dkey            null,
    applicationField1               ...;
    applicationField2               ...;
    applicationField3               ...;
```

FIG.2

```
Create view foo
as
select dkey, applicationField1, applicationField2, applicationField3
from x#foo
where omitChar = ";"
```

*FIG.3*

Status

| visitID | assigned | report | validated |
|---|---|---|---|
| 7 | 0 | 0 | 0 |

*FIG. 4A*

Status

| visitID | assigned | report | validated |
|---|---|---|---|
| 7 | 1 | 0 | 0 |

*FIG. 4B*

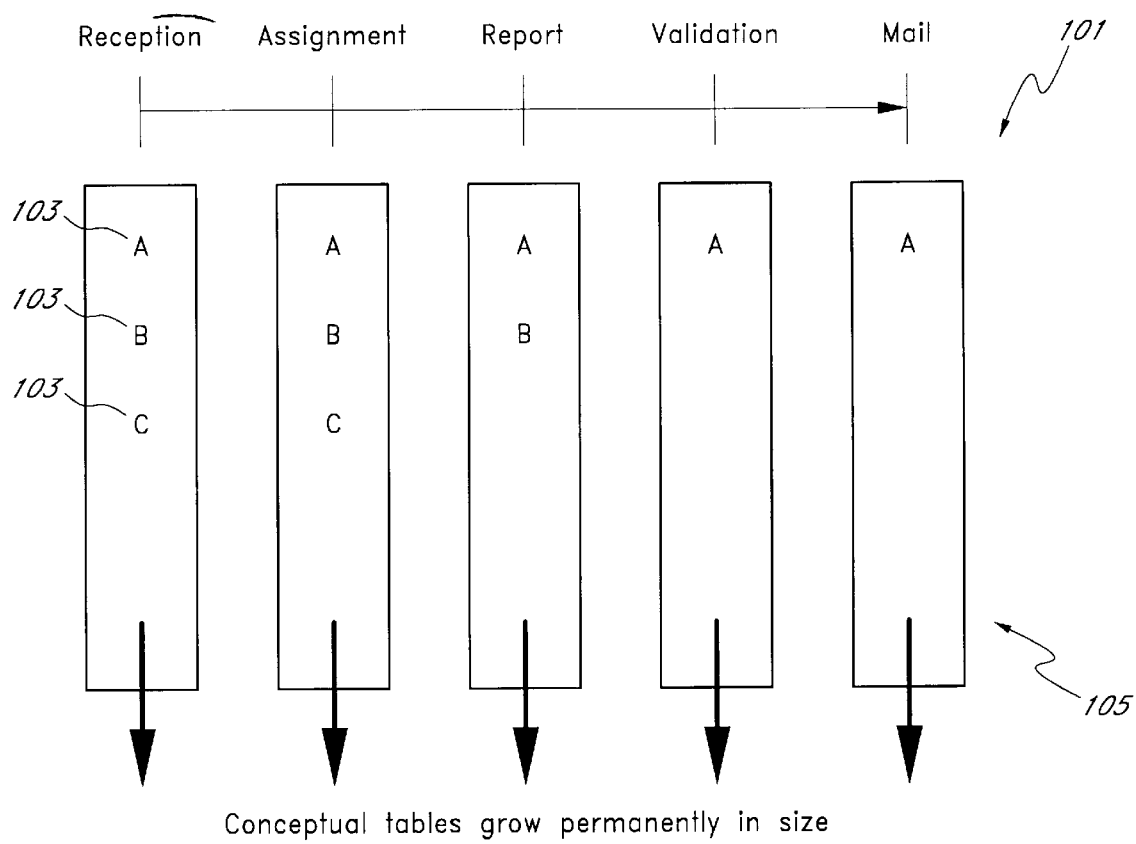

Conceptual tables grow permanently in size

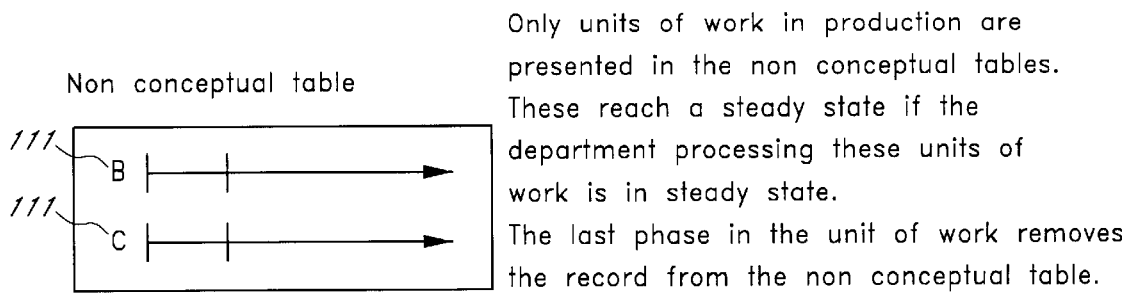

Non conceptual table

Only units of work in production are presented in the non conceptual tables. These reach a steady state if the department processing these units of work is in steady state.
The last phase in the unit of work removes the record from the non conceptual table.

Two units of work are in production: B and C. The record representing A has been removed from the non conceptual table since this unit of work is completed.

FIG. 5

```
select name = (rtrim(p.patName) + " " + rtrim (p.patFirstname)),
       r.ctype, r.afdeling,
       doctor = u.firstname + " " + u.name,
       v.verslagNr
from   doctorSup a, receptie r, patienten p, verslag v, s9User u
where  a.usernameSup = "x163646" / *username of the supervisor */
and    a.cnr       = r.cnr
and    r.eadnr     = p.eadnr
and    a.cnr       = v.cnr
and    not exists
           (select *
            from validatie va
            where va.verslagNr = v.verslagNr)
and    v.typeVerslag = "eindverslag"
and    a.usernamedoctor = u.loginname
```

FIG. 6

```
select name = (rtrim(patName) + " " + rtrim (patFirstname)),
       ctype, afdeling,
       doctor= u.Firstname + " " + u.name,
       v.verslagNr
from   statusContact s, verslag v, S9User u
where  s.usernameSup = "x163646"
and    s.cnr         = v.cnr
and    s.verslag     = 1
and    v.typeVerslag = "eindverslag"
and    s.validatie    0
and    s.usernamedoctor  u.loginname
```

*FIG. 7*

```
/*Part 1*/
select    cnr, usernameArts
into      #validated
from      doctorSup
where     usernameSup  = "x163646"

/*Part 2*/
delete    #validated
from      #validated a, verslag v, validatie va
where     a.cnr         = v.cnr
and       va.verslagNr  = v.verslagNr
and       v.typeVerslag = "eindverslag"

/*Part 3*/
select    name = (rtrim(p.patName) + " " + rtrim (p.patFirstname)),
          r.ctype, r.afdeling,
          doctor = u.Firstname + " " + u.name,
          ve.verslagNr
from      #validated v, verslag ve, receptie r, patienten p, S9User u
where     r.eadnr          = p.eadnr
and       r.cnr            = v.cnr
and       v.usernamedoctor = u.loginname
and       ve.cnr           = v.cnr
and       ve.typeVerslag   = "eindverslag
```

FIG.8

Workstation　　　　　Application server　　　　Database server
Windowing server　　Windowing client (X-Windows)　(Sybase)
(X-Windows)　　　　System 9 (Prolog)
　　　　　　　　　　Database client (Sybase)

Workstation　　　　　Application server　　　　Database server
Windowing server　　Windowing client (X-Windows)　(Sybase)
(X-Windows)　　　　System 9 (Prolog)
　　　　　　　　　　Database client (Sybase)

```
xTmplDef(doctorSup,
  true,
  (XmNtitle = 'Toewijzing doctor supervisor',
   XmNx=320, XmNy=320, XmNheight=270, XmNwidth=620],
  [(zoekSup, [callback (XmNactivateCallback)=zoekSupCB$artsSup)),     ← Name of the widget
   (usernameSup,
     [flushOnLeave = [nameSup, FirstnameSup],
      callback(XmNactivateCallback) = zoekSupCB$artsSup]),            ← List of parameter=value
   (nameSup,                                                              for this resource
     [flushOnLeave = [usernameSup, FirstnameSup],
      callback(XmNactivateCallback) = zoekSupCB$doctorSup]),
   (FirstnameSup,
     [flushOnLeave = [usernameSup],
      callback(XmNactivateCallback) = zoekSupCB$doctorSup]),
   (zoekdoctor, [callback(XmNactivateCallback)=zoekdoctorCB$doctorSup]),
   (usernamedoctor,
     [flushOnLeave = [namedoctor, Firstnamedoctor],
      callback (XmNactivateCallback) = zoekdoctorCB$doctorSup]),
   (namedoctor,
     [flushOnLeave = usernamedoctor, firstnamedoctor],
      callback (XmNactivateCallback) = zoekdoctorCB$doctorSup]),
   (Firstnamedoctor,
     [flushOnLeave = [usernamedoctor],
      callback (XmNactivateCallback) = zoekdoctorCB$doctorSup]),
   (additionalSupPB
      callback (XmNactivateCallback) = addSupCB$doctorSup]),
   (supervisorPB, [callback (XmNactivateCallback) = supervisorCB$doctorSup])
```

FIG. 13

```
┌─ Selector ──────────────────────────────────────────────┐
│  ┌────────────────────────────────────────────────────┐ │
│  │ I  Typing in this field allows to search the graph for a pattern> │ │
│  ├────┬───────────────────────────────────────────────┤ │
│  │ -> │ Rx search top 20 (Oncologie)      +           │ │
│  ├────┼───────────────────────────────────────────────┤ │
│  │ -> │ Rx search general                             │ │
│  ├────┼───────────────────────────────────────────────┤ │
│  │ -> │ Activity boom (Oncologie)                     │ │
│  ├────┼───────────────────────────────────────────────┤ │
│  │ -> │ Top afdeling GEZ                              │ │
│  ├────┼───────────────────────────────────────────────┤ │
│  │ -> │ general start                                 │ │
│  └────┴───────────────────────────────────────────────┘ │
└─────────────────────────────────────────────────────────┘

┌─ Selector ──────────────────────────────────────────────┐
│  ┌────────────────────────────────────────────────────┐ │
│  │ I                                                  │ │
│  ├────────────────────────────────────────────────────┤ │
│  │    │ Rad: RX Thorax (rx th)    +                   │ │
│  │    ├───────────────────────────────────────────────┤ │
│  │    │ Rad: RX Ribbenrooster (rx rib)                │ │
│  │    ├───────────────────────────────────────────────┤ │
│  │    │ Rad: RX Mammografie (rx mammo)                │ │
│  │    ├───────────────────────────────────────────────┤ │
│  │    │ Rad: RX Lumbale spine (rx lwz)                │ │
│  │    ├───────────────────────────────────────────────┤ │
│  │    │ Rad: RX Kahler skeleton (axial skeleton en lange beende │ │
│  │    ├───────────────────────────────────────────────┤ │
│  │    │ Rad: RX Dorsale spine (rx dwz)                │ │
│  │    ├───────────────────────────────────────────────┤ │
│  │    │ Rad: RX Cervicale spine (rx cwz)              │ │
│  │    ├───────────────────────────────────────────────┤ │
│  │    │ Rad: RX Pelvis (rx bekken)                    │ │
│  └────┴───────────────────────────────────────────────┘ │
└─────────────────────────────────────────────────────────┘
```

FIG. 14

KWS Formuller

Activity System

KWS-TESTPATIENT NUMMER 14   189579

MAT Admission date   194883   460830M999

Supervisor

| x197156 | xxxxx | Additional supervisor | xxxxxx | ? |
| x285685 | xxxxx | | xxxxxx | ? |

Gynecological Echograph

Code: / /

Applicant x285596
Supervisor x163646
Anethesiologist
information
Room/Bed

Application Date 12-01-1996 18:17
Scheduled Date 12-01-1996 0:00 act

Request for data

Type of ultrasound
Indication
Last period

Points of special attention

OK    cancel

FIG. 20B

| (Sub)department | Pediatrics | | | | Oncology | | | |
|---|---|---|---|---|---|---|---|---|
| Supervisor | W | | X | | Y | | Z | |
| Physician | A | B | C | D | E | F | G | H |
| Time | Duration | | | | | | | | |

FIG. 25

RELATIONAL DATABASE COMPILED/STORED ON A MEMORY STRUCTURE PROVIDING IMPROVED ACCESS THROUGH USE OF REDUNDANT REPRESENTATION OF DATA

This application claims the benefit of provisional application 60/018,140 filed May 22, 1996.

FIELD OF THE INVENTION

The present invention is related to a relational database compiled/stored on a memory structure and adapted by access by application programs executing a query within said database.

The present invention is more precisely related to a system for developing software to be compiled in said computer.

BACKGROUND OF THE INVENTION

A database takes much of the burden of storing and managing data out of the application.

The advantages of using a database are manifold. The most important are: centralized control of data storage, sharing of data (between applications and users), centralized security, concurrency control, reduction of redundancy, . . .

Database management systems are commercially available for virtually any computer platform. The technology has proven itself and it is cost effective to use a database. The alternative to using a database is using computer files to store the data. The application becomes responsible for each of the database tasks mentioned above. Usually this option is only taken if there is no need for concurrency control, data sharing, security, . . . This is almost only the case in single user (PC) systems.

There are several approaches possible in building a database management system, but the most important is the relational approach. Relational database management systems became commercially available in the late 1970s. Their main advantage over existing database technology was that they simplified the view the user had of the data. A very loose definition of a relational database management system is given as follows: a relational system is a system in which the data are perceived by the user as tables (and nothing but tables); and the operators at the user's disposal (e.g. for data retrieval) are operators that generate new tables from old. This definition looks at a relational database management system from the user's point of view. The actual storage format of the data is of course much more complicated. But this shows the main advantage of relational systems: the user only deals with the simplified view and is completely shielded from the lower level implementation structures.

The vendors of relational systems have standardized the way to access a relational database. Practically all databases support SQL (Structured Query Language). SQL is the language with which the user can create new tables from existing ones. SQL is a declarative language: the users specifies what data need to be retrieved and from what tables but not how they need to be retrieved. Since the user has no knowledge of the underlying physical data structures, it is impossible for him to decide how the data should be retrieved. Therefore the system needs to translate each SQL statement into a query path. This specifies how the physical structures are accessed to retrieve the data.

Usually many query paths are possible for one SQL query. Almost all relational systems now have a component called the query optimizer. The query optimizer selects the path that will probably produce the desired result in the shortest time. To speed up the retrieval of data, the database administrator can define indexes. An index is a data structure that stores all values for a particular column in some table and keeps a reference to the rows containing that value. The values are stored in a structure that allows fast retrieval of a particular value. If a user wants to retrieve all the rows containing a specified value, the system can look up the value in the index, retrieve the references to the rows containing that value and use those references to directly retrieve the rows. This will be faster than scanning the whole table and checking each row for the specified value, because the index is smaller, the index is structured so that the relevant value can be retrieved without scanning the whole index. The main performance increase comes from reducing disk accesses. The disk is a mechanical device and is slow as compared to access to internal memory. Indexes are hidden from the user and the results of the query are the same whether the indexes were used or not.

The query optimizer decides which indexes will be used and in what order. To take this decision the query optimizer takes into account the length of the tables, the availability of indexes, the selectivity of the index, . . . It will always try to reduce the amount of rows to retrieve as early as possible in the query. The selection of a query path is done using heuristics so it can not be guaranteed that the optimizer will produce the optimal path. As it will be seen later on, the optimizer often does not have enough information to produce the optimal path. This is often the case for complex queries and then one can aid the optimizer by splitting the query in smaller parts which are easier to optimize.

Problem Definition

If a data model "shapes one's view and limits one's perceptions" then those limitations have to be as few as possible and the shaping should not be distorting. This shaping and limiting of the view of the world is in part a preferred effect: it structures one's world view and puts the focus on that part of the data to be manipulated using a computer. Therefore a data model is subject to three major forces:

the desire to model a defined world of interest as completely as possible, the structure to impose on this model of the world, and the limitations of the level of complexity in relation to the hardware and the software.

With time reality changes as do one's views of this reality. For these reasons data models might have to be changed during the life time of an application. Updates of the data model are costly in terms of human resources. Thus a data model should also be time-resistant.

The model should also allow for any data structure to be entered since a limitation of what can be entered would also limit one's world view through the model. That way all information can be captured without distortion and different models can be deduced from these raw data. The model is only deduced from the raw data. No part of the model is implied or enforced by the internal data structures since any type of structure can be entered. If the model is only deduction this also makes it time resistant. To change the model one "only" has to change the deductions, not the data representation. Another advantage is that several models can be deduced (and used) at the same time on the same raw data. Since the data are truly "raw", that is not distorted to accommodate the structure of the internal data representation, these data can be seen as truths or essences: somebody at a certain point in time has stated that X was true. Entering data is adding a message to a gigantic pool of messages. The world is chaotic and the structure of the chaos to model is in the eye of the beholder. The problem is that the less information in the data representation, the more information needs to be deduced. If there is no structure inherent in the internal data representation this becomes a gigantic task. One trade freedom of storage for complexity of deduction. Current database technology does not allow this freedom of storage.

Relational databases are state of the art but have a much more rigid storage format than described above. In a relational database data are represented in the form of tables. A table has columns and the rows which are called records or tuples. So for each type of message a table is defined to store all the messages of that type. A message becomes a row in that table. Tables have to be defined before data can be stored in them. This limits the freedom: to foresee which types of messages will be needed. Because the structures have to be created beforehand, the users cannot add messages that where not anticipated. Using a query language the programmer can deduce new virtual tables (called "views") from other tables. A query is the deduction of a set of tuples (view) from several other sets of tuples (tables and views). A typical database can handle queries that use up to 16 tables, but a query with 16 tables will be far too slow to use in an on-line interactive system. This severely limits the level of complexity of the deductions possible for queries that require fast response times.

It is an option to choose data modelling strategy that captures all raw data. This is done in the form of messages. A message is the content of an electronic form. The messages are in essence statements or essences and have the implied generic form of "user X at time Y states that Z is true". This implies that the data model is additive: new information is added as a new message. Messages are never updated: a message that is true at a certain point in time will later always have been true at that point in time. A new message might contradict or supersede an old message but the statement the old message stands for, remains true. So updating is conceptually not allowed in this data modelling strategy. There is one reason why updates are allowed here: the user is fallible and might make a (typing) error when adding a message to the system. These errors need to be corrected. The solution is to send another message of the same type to the database and to state that the new message is a correction of the previous one. The old message is only logically deleted, i.e. in the deduction of the present model in most cases a message is ignored whenever there exists another message that corrects it. At the interface level the user can correct the content of the electronic form and with one mouse-click send the new message. The system automatically omits the old version logically and links the new version to the old.

According. to this option the database will grow while query performance degrades. This is a bottleneck related to unlimited database growth. The next bottleneck that will arise is recovery time. The larger the database, the longer it takes for back up or to reload it from tape in case of media failure.

SUMMARY OF THE INVENTION

In order to have a clear vision of the main characteristics of the present invention, several definitions are given hereunder.

Conceptual tables are tables of a first set of tables which can be modified by adding another tuple with data to the table.

Non-conceptual tables are tables of a second set of tables which can be modified by whatever action, e.g.:
update of one column of a tuple
addition of another tuple
update/change of one tuple
deletion of tuples
etc.

In the present invention, data can be defined as:
a tuple,
a column,
an element on the cross of a column and a tuple, or
parts thereof.

Database management systems store meta-data, this is data about data. These data are kept in the data dictionary. Typical meta-data are the types (character, integer, real number, . . . ) for each of the columns in a table. Meta-data are used by the system to check for errors.

Redundant should be understood as:
a copy of data,
a "derivation" of any data like
   an operation (multiplication, division, percentage, combination, verifying the presence of, . . . ) on any data, only using one data point,
   an operation (multiplication, division, percentage, combination, verifying the presence of, . . . ) on any data, using several data points (tuples, columns in the same table or in several tables).

An application can be defined as a set of programs that integrate a specific functionality.

A service can be defined as any act that can be asked for or executed by a patient. For instance, a service type can be any act of radiology or nursing.

Finally, a unit (or unit of work) is a unity of acts that are executed in a specific order (the unity is made by the unity of patient, the unity of treatment, the unity of service, . . . ).

The present invention is first related to a relational database compiled/stored on a computer environment and adapted for access by application programs executing a query within said database and compiled/stored on said computer environment comprising:
a first set of tables with first columns and tuples containing first data;
a second set of tables with second columns and tuples containing second data, each of said second data being a redundant representation of at least one of said first data.

A second object of the present invention is related to a method for executing queries within a relational database, comprising the steps of:
selecting tuples in said second set of tables, and
reading out the tuples of said first set of tables corresponding to said selected tuples of said second tables.

A third object of the present invention is related to a database access system compiled on a computer environment, comprising:
a relational database including
   a first set of tables with first columns and tuples containing first data,
   a second set of tables with second columns and tuples containing second data, each of said second data being a redundant representation of at least one of said first data; said database being adapted for access by application programs executing a query in said database;
meta-data; and
means for optimizing the steps of accessing said database, said means comprising tools for retaining a set of meta-data after first data are inserted in said database, said set of meta-data verifying errors in an insertion of next first data in said database.

A fourth object of the present invention is related to a clinical workstation implementing on a computer environment a representation of a group of processes, operations, services, acts, objects and persons within a hospital comprising:

a relational database having:
- a first set of tables with first columns and tuples containing first data, said first data being electronic messages being the contents of electronic forms wherein said first set. of tables is organised as a set of generalized tables according to the different types of said operations;
- a second set of tables with second columns and tuples containing second data, each of said second data being a redundant representation of at least one of said first data;

software modules, integrating a medically logical unit of said hospital.

a user interface including a dashboard and integrating said modules; and a generator stored on said computer environment comprising:
- first tools supporting a user interface;
- second tools accessing said database;
- third tools implementing said electronic messages and linking said database with said user interface whereby said messages are stored as data in said database and whereby said messages can be entered or accessed via said user interface.

A fifth object of the present invention is related to a hospital information system stored on a network of computers an workstations comprising:

a relational database stored on at least one computer of said network comprising:
- a first set of tables with first columns and tuples containing first data, said first data being electronic messages being the contents of electronic forms;
- a second set of tables with second columns and tuples containing second data, each of said second data representing at least one of said first data;

a generator stored on at least one computer of said network comprising:
- first tools supporting a user interface;
- second tools accessing said database;
- third tools implementing said electronic messages and linking said database with said user interface whereby said messages are stored as data in said database and whereby said messages can be entered or accessed via said user interface; and
- at least one clinical workstation comprising said user interface and modules allowing for entry of essences consisting of the group of processes, operations, services, acts and objects related to a patient's medical file within the hospital.

More particularly, the present invention will be described in relation of a clinical workstation and its integration within an existing administrative system to form an hospital information system.

It was decided not to build each application separately but to construct a basic software layer (the generator) on top of which applications were built. The generator consists of three main modules, one to handle the graphical user interface, one to handle database access and one to incorporate the basic user interface paradigm. This last module functionally ties the two other modules together.

According to a preferred embodiment of the present invention, the generator uses Sybase as database, Prolog as application language, MacWorkstation and later X-windows for the graphical user interface.

The purpose of the generator is:
- to shield the applications from the underlying software components. This diminishes the dependence on them;
- to provide a higher level functional interface for these components. This allows faster application development since it allows to use larger building blocks;
- support for a basic user interface and data modelling paradigm. Including this in the generator causes all applications to share these common features. This makes the system more user friendly and easier to master.

A new data modelling strategy is disclosed hereunder. This strategy discerns two types of data tables:
- conceptual tables are known to the application and its users. They model the world of interest.
- non-conceptual tables do not exist from a user point of view. They contain redundant data and embody an alternative data model.

Both performance and design benefit from separating tables in two classes:
- performance is enhanced by giving the non-conceptual tables a data model that facilitates those queries that are not performant when run on the conceptual tables. Usually, only the minimal information necessary to speed up those queries are stored;
- design is facilitated because less performance compromises need to be made in building the conceptual data model. Using this technique the design for expressivity is separated from the design for performance.

For the preferred embodiment of the present system application according to the present invention (called conceptual model of system 9), several specifications were developed:
- the data model is deletionless; that is, data are never physically deleted, only logically.
- the data model is additive. This means that updates are conceptually not allowed in the model. Data entry is seen as true statements (messages) from a user. The data model is a set of tables to hold structured messages. Normally a message does not need to be corrected unless an error was made. Since the model is deletionless both versions of the message are kept when it is corrected.

The present system conceptual model according to the present invention consists of three different levels:
- the physical level hosts all data whether logically deleted or not;
- the conceptual level is defined on top of the physical level and shows the current version of the messages. This is the level the generator operates on;
- the application level defines the relationships between the messages.

These four data models (the three conceptual levels and the non-conceptual tables) form a meta-model. The use of the meta-model facilitates reasoning over the global data model: the generator and the application operate on different levels of the conceptual model and performance problems are solved in the non-conceptual tables. Each model has a specific function in the whole of the application.

During the development of the system, the electronic form was chosen as the basic interface object. The user interacts with the system by sending and viewing electronic forms. This electronic mail-like metaphor matches well with a deletionless and additive data model. The basic form operations are implemented in the generator and do not need to be implemented in each application.

As an essential element in the user interface the dashboard was developed. The dashboard is the main instrument to navigate between different functions of the electronic medical record for a patient. It was developed for the first present system application, and was repeated in all subsequent applications. In a way the dashboard bundles the data for a patient and creates a virtual electronic medical file.

To solve the problem of implementing the diversity inherent to order entry, a generic tool is developed that it forms the basis for all order entry. Several subproblems were solved:

an interface paradigm consisting of a selector, an editor and a collector was developed. These three items interact in a standard way in all order entry applications. Rule bases are used to steer the behaviour for specific functionality;

the logical data structures used to represent orders in this system needed to be translated to the more rigid relational format. All structures are stored in a set of four tables by translating them to a canonical format using a rule base. Thus the diversity of order entry can be handled without creating an unmaintainable number of database objects.

The generator which is disclosed here supports the user interface metaphor and data modelling strategy. It is the basis for all three clinical applications implemented. This demonstrates the general applicability of the tools and the metaphors used.

BRIEF DESCRIPTION OF THE DRAWINGS

FIG. 2 is an illustration of a definition of a system database table.

FIG. 3 is an illustration of a definition of a table-view foo.

FIGS. 4a, 4b are illustrations of status tables.

FIG. 5 is an illustration of a use of non-conceptual tables.

FIG. 6 is an illustration of a validation list—query 1.

FIG. 7 is an illustration of a validation list—query 2.

FIG. 8 is an illustration of a validation list—query 3.

FIG. 13 is an illustration of a MotifShell data structure to add features to widgets.

FIG. 14 is an illustration of options for browsing of a graph.

FIG. 15 is an illustration of an interaction of form, table, table-view and r"view.

Figure 18:
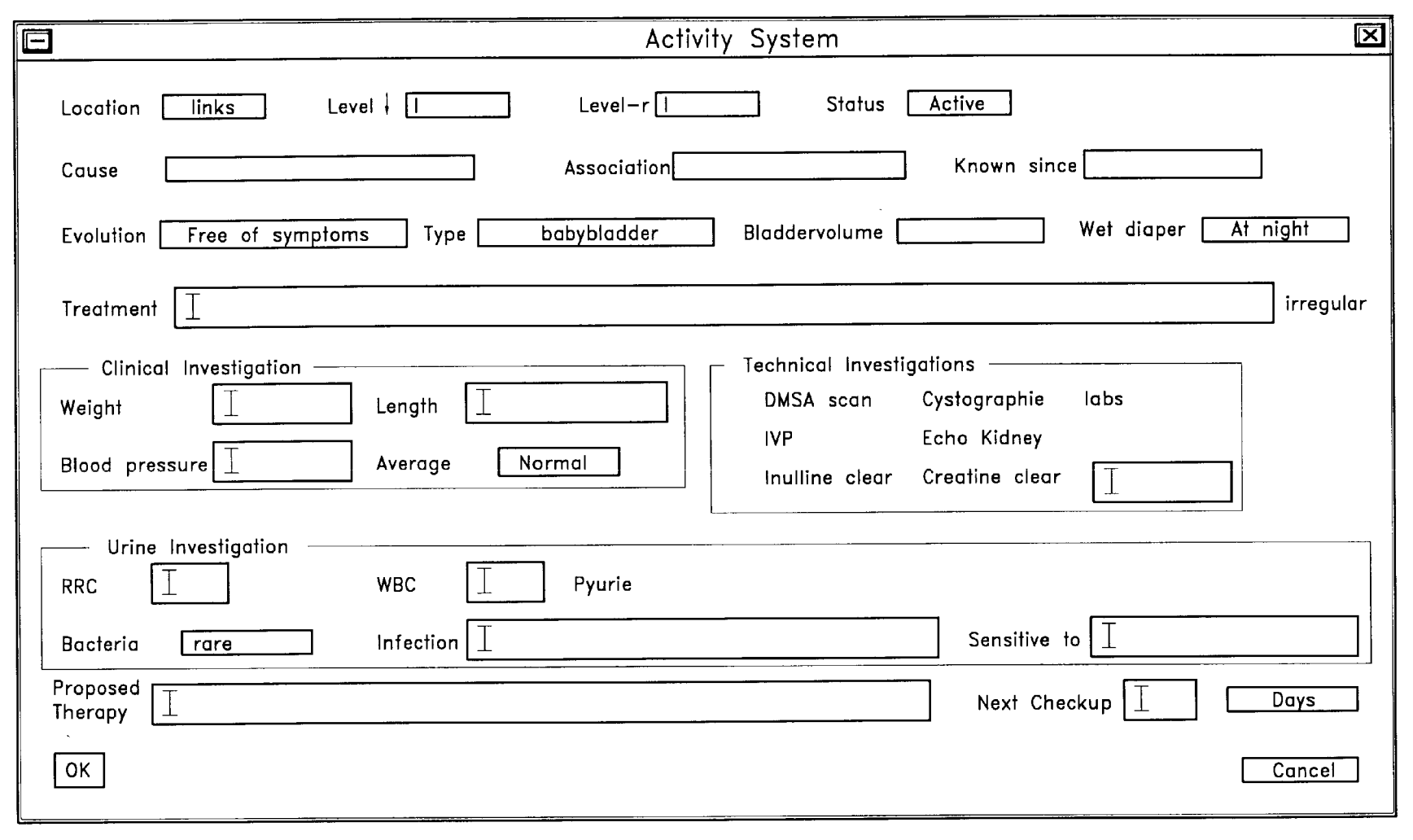

FIG. 18 is an illustration of parameters asked to generate a report for vesico urethral reflux.

Figure 20A:
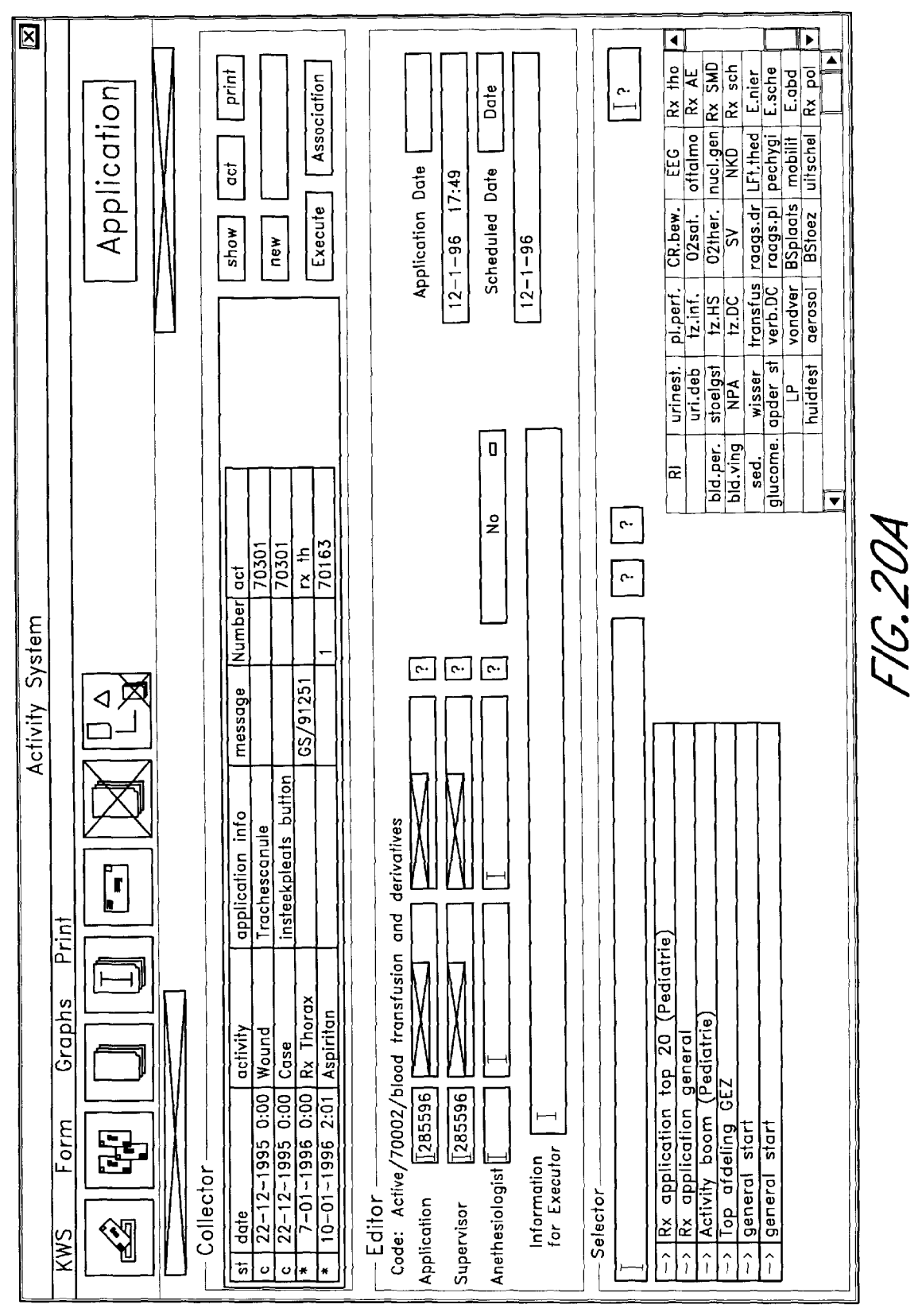

FIG. 20 is an illustration of a service manager.

Figure 25:
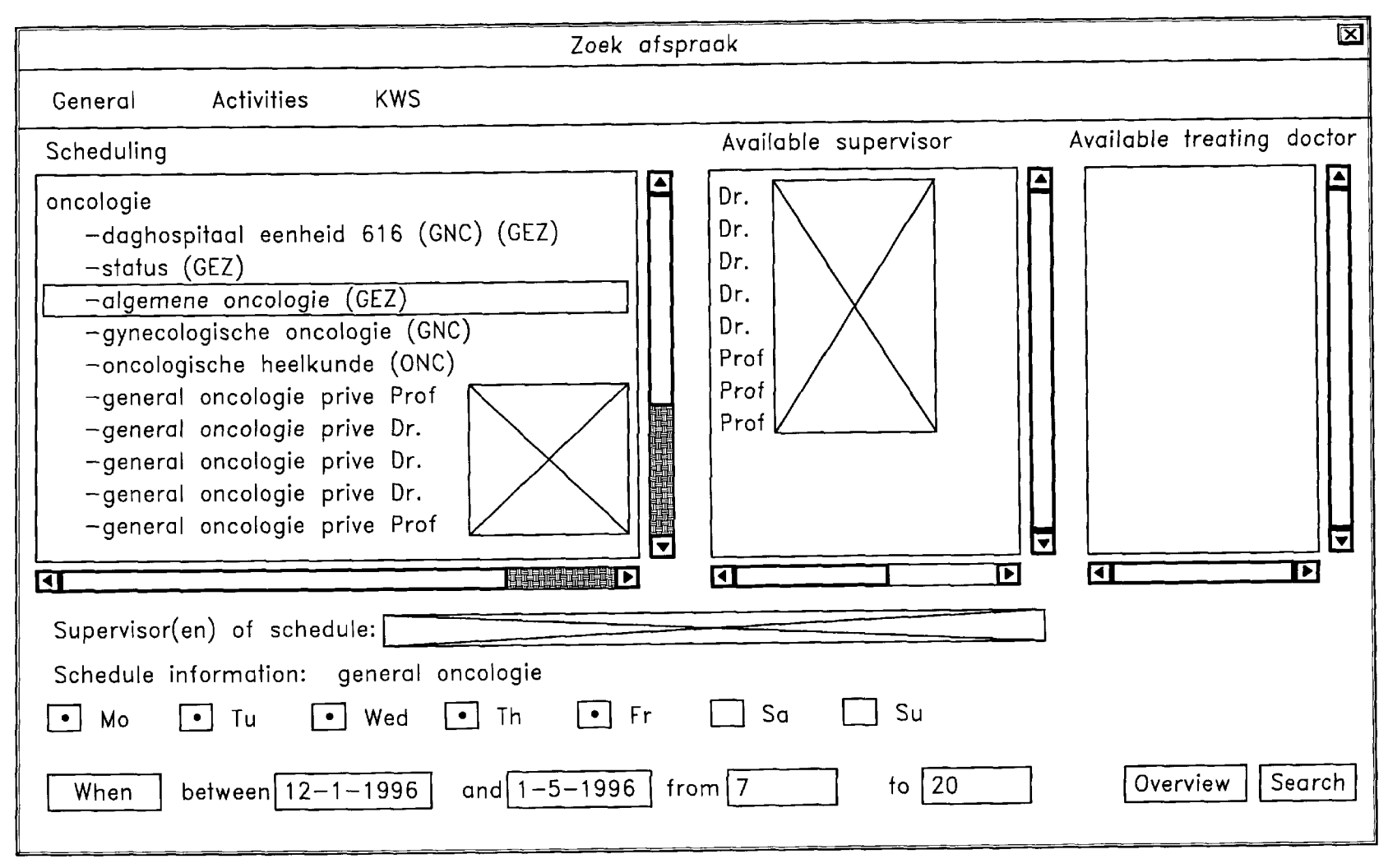

FIG. 25 is an illustration of a search window of the appointment system.

Figure 1:
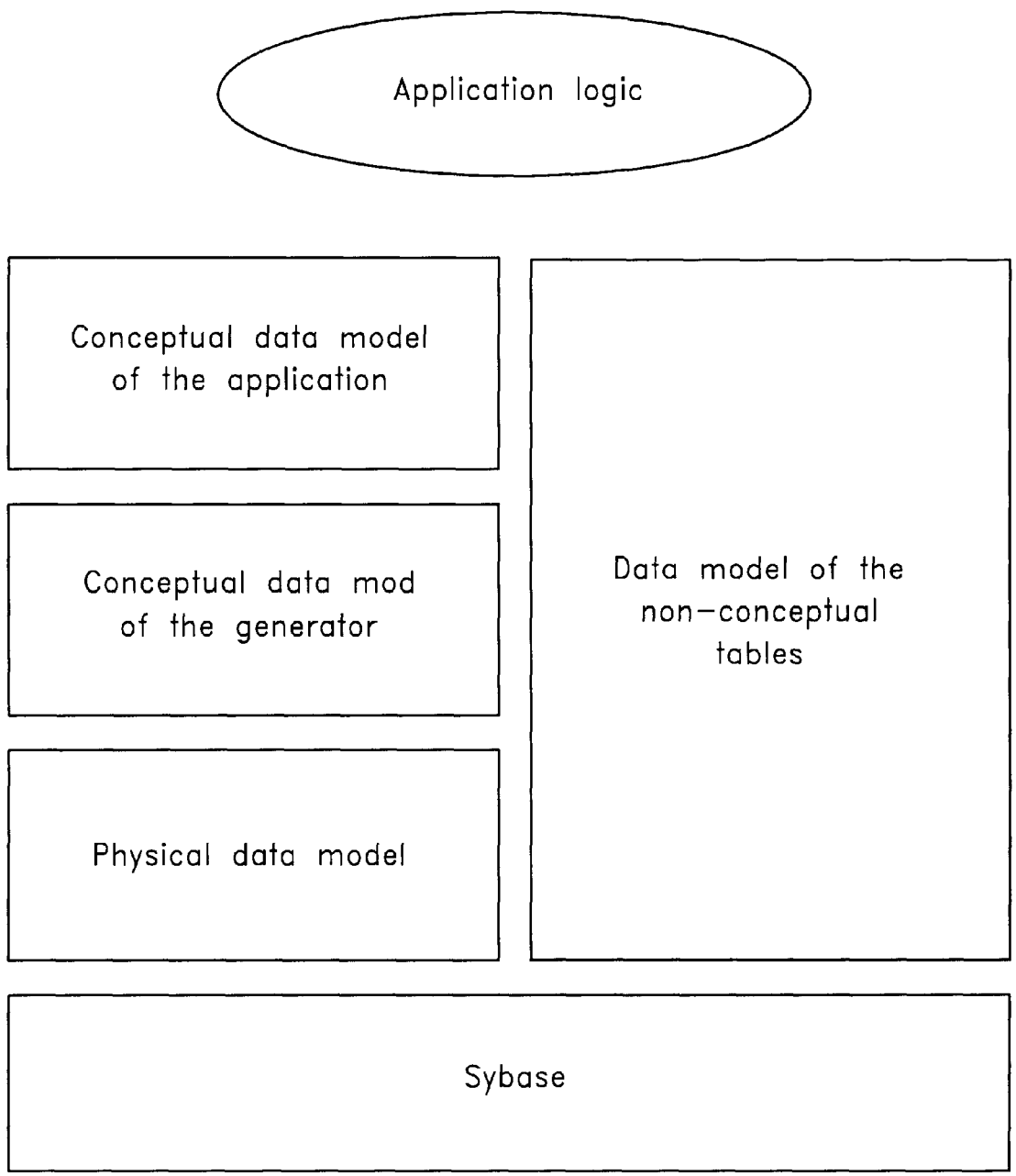
FIG. 1 is an illustration of a data model architecture.

For the clinical workstation, it is identified the generic functionality that is needed in the clinical departments. This was implemented in the base modules. The specificity of each department was handled using rule-bases. Several software libraries to handle these rules where developed. The system was for instance applied in Paediatrics and afterwards in the Oncology, Gynaecology/Obstetrics and Ear-Nose-Throat departments. No major changes where necessary to the base modules to cater for the differences between those departments. All differences could be handled by adapting the rule base.

To avoid fragmentation of clinical data, a global hospital information system plan is required. This system should be able to handle both the administrative and the clinical data in an integrated way. A clinical workstation would need to be built or bought as an addition to the administrative system. The clinical workstation was to be the clinician's interface to the hospital information system. It should be able to capture clinical data at the source. These data should be the basis for an electronic medical record. The system should allow the use of data for management purposes at the departmental and hospital level.

DETAILED DESCRIPTION OF THE INVENTION

The further textual specification assumes for the purpose of teaching only the implementation of a system developing software to be compiled on a set of computers and more particularly for a hospital information system stored on a network of computers and workstation.

Sybase was the one of the first relational database management systems to gear itself towards OLTP (On-line Transaction Processing). In OLTP applications many transactions are requested per second and the number of simultaneous users is high. Sybase pioneered some features that warranted its selection as the main clinical database.

The Sybase server consists of a single UNIX process. This means that all simultaneous users are catered for by this single process. The advantage is that this process can do an overall optimization of memory management and disk accesses for all user processes. Originally, most of the competition relied on several processes to implement the server. This left much of the scheduling to the operating system which is easier to implement but less efficient because the operating system has less information to base its scheduling on. The operating system does not "know" what the processes it schedules are doing and what their interaction is. By bringing all user processes into one server process, this server process can take advantage of the interdependencies of the user processes to schedule them.

With Sybase the client software is only a C library. This C library can be incorporated into the application program. All accesses to the database server are made via calls to programs in this library. The client software does not process data. It only sends the commands to the server and retrieves the resulting rows. All other processing is done on the server. This architecture allows to run the application and the database on different servers. The best results are obtained when Sybase has its own dedicated server, and all clients reside on another machine.

In Sybase SQL queries can be written as a procedure. Such a procedure can have parameters to pass attribute values to the query. Procedures can be compiled and stored on the server. To enhance expressivity, Sybase added procedural control statements (if . . . then . . . else; while loops) to SQL. This allows to some extend to write smaller programs as stored procedures on the server. There are several advantages to this approach:

compilation and most of the optimization is done when the procedure is created. This speeds up retrieval when the procedure is called. For procedures that are called thousands of times per day this also reduces overall load on the database server;

network traffic is reduced because only the procedure name and parameters are sent from client to server;

more access control. Users can be allowed to execute stored procedures without giving them access to the underlying tables. This gives complete control over which queries the user is allowed to perform. If necessary the procedure can perform (complicated) authorization checks before executing the actual query;

if the query is reformulated, the application does not need to be recompiled as opposed to (some implementations of) embedded SQL.

Triggers are a special form of stored procedure that are executed when an insert, update or delete is done on a table. Triggers are executed within the same transaction as the operation that fired them. Triggers can perform business rule checks and if the check proves the operation invalid, the trigger can force the transaction to roll back (i.e. to undo all changes since the transaction started). Triggers are extensively used to perform consistency checks and to support the specific fields and tables of the present system data model. Application Development Language and for the Purpose of Teaching Only in the Sequel is Chosen: Prolog A computer is programmed using a computer language. At the lowest level the processor executes instructions. The set of instructions that the processor can execute is defined by the manufacturer when the processor is designed. The manufacturer also supplies a language that uses these instructions to program the processor. Such a language is usually called an assembly language. Assembly language is hard to read and to program because it is a low level language. Its expressivity is low; that is, even simple programs require many instructions. Applications are rarely written in assembly language. Usually so-called third generation languages are used to program applications. A program in these languages is transformed (compiled or interpreted) into assembly language instructions which are then executed by the processor. Examples of third generation languages are Pascal, C, COBOL, PL/1 and FORTRAN. These languages are more expressive than lower level languages. All but non-trivial programs are much shorter in C or Pascal than they would be in assembly language. This means that the burden of part of the complexity of programming has been shifted from the programmer towards the compiler (or interpreter). The more expressive the language, the more complex the compiler or interpreter for such a language. The compiler or the interpreter needs to be more "intelligent" to be able to transform a program written in this language into an assembly language program.

Before the start of the project, the U.Z. Leuven used the third generation language COBOL in its administrative systems. At that time fourth generation languages were emerging. These were more expressive and compensated the increased complexity of the implementation by being more specific. They are usually very well integrated with relational database systems and very apt at retrieving and manipulating data from these databases, and come with a built-in graphical user interface. The main disadvantage of these languages is that they are owned by the company that built them, which makes them dependent on the financial fate and the commercial vagaries of the parent company. Another disadvantage is their specificity. The complexity of the implementation is reduced by making them more specific. Most fourth generation languages are geared towards database access. This makes non database computations often difficult to program (and the resulting program is usually not very efficient).

An alternative to fourth generation languages is Prolog. Its main advantages over fourth generation languages are:

it is not owned by a single company, and it is a general programming language with high expressivity.

Prolog is often called a fifth generation language but this term is misleading. Prolog did not evolve from fourth generation languages but has its roots in logic. The language is an implementation of a subset of first-order-logic called Horn clauses. Many implementations of Prolog are available and as of June 95 an ISO standard is defined.

Prolog has become a performant language because most of the research into the optimization of Prolog is done by many universities and the ideas resulting from this research are then built into the specific Prolog compilers. As with relational databases, there is competition between the Prolog vendors for the fastest Prolog. With a fourth generation language only one company can do all the work.

Prolog by BIM is used, which is both fast and robust. It has been decided at the start of the project to do all developments in Prolog and to translate the time critical parts into C when necessary. This was never needed: the Prolog programs are sufficiently fast.

Prolog is not the "silver bullet" to solve the so called chronic software crisis, but it has some unique features that make it easier to write programs with less bugs.

Memory Management

A program manipulates data structures. Usually the programming language has specific instructions to allocate memory to data structures that it wants to create. When the data structures are no longer necessary the program de-allocates the memory. A frequent type of bug is a memory leak. When a program does not de-allocate all the memory it no longer needs, it may stop functioning when all memory is consumed. In large programs these bugs may be hard to find since the error (not de-allocating memory) does not immediately cause the program to fail. If the program does not run continuously the error may never be detected since the program never exhausts available memory. In a clinical workstation that is operative day and night even a memory leak of one byte will eventually cause the system to fail. In Prolog memory is allocated automatically and when practically all memory allocated to the program is used, a garbage collector is invoked. The garbage collector detects memory that belongs to data structures that are no longer needed and de-allocates it. This eliminates an important source of bugs.

No Dangling References

Most programming languages use pointers. A pointer is an electronic reference to a data structure. If the structure has been deleted (due to memory de-allocation) or if the program wrongfully altered the reference, the pointer points to random bits or to another structure if the memory was re-used. This is called a dangling reference. This problem cannot occur in Prolog since Prolog does not use explicit references. All references are implicit and handled by the Prolog language internally. The programmer can manipulate data structures via variable names and does not (need to) know where the structure resides in memory.

The Logical Variable

Logical variables are variables that can be free (i.e. they did not yet receive a value) or instantiated (i.e. a value was assigned to the variable). Destructive assignment (i.e. re-assigning a value to an already instantiated variable is not possible. In most other languages destructive assignment is the rule rather than the exception.

The omission of destructive assignment facilitates debugging. In a large team people constantly use pieces of software written by other members of the team. To put it simply, you give your data structures to somebody else's program that reads them (maybe alters them) and that creates some new structures for you. If the function is faulty, it may destroy your data structures, your program will probably not notice this immediately but will encounter problems later on when it tries to do something with these structures. Depending on the alteration, the program may calculate wrong results or halt completely. In most languages, parameters are passed as references.

Because Prolog does not allow destructive assignment any faulty data structure can only be created faulty and not be inadvertently damaged. This facilitates debugging since one programmer does not need to trust the other programmer's functions: he cannot change his data structures.

Formal Specifications

One of the methods to write reliable software is to construct correctness proofs for each program. This is only feasible for very small programs and checking the correctness of the proof can be as tedious as checking the correctness of the program itself. Some languages try to overcome this by allowing pre- and post-execution conditions to be specified in a formal logical way. Since Prolog is a declarative logical language the program is the formal specification. It is an executable specification. Although this is an oversimplification—Prolog allows some non-logical operations—large parts of the program can be read completely declaratively. Especially the rule bases used to customize the modules for the different departments.

Using Artificial Intelligence (AI) Techniques

Prolog also allows to use Artificial Intelligence technology to build the present system environment as well as seamlessly integrating it with the general clinical workstation application. Many techniques developed in and for Artificial Intelligence were used. These techniques also make reliable, flexible and maintainable programs with shorter development times than with conventional languages. Some of these techniques are discussed here but it will be elaborated on their specific use when describing the software modules in which they occur.

Rule Based Systems

A common technique in expert systems is splitting the software into an inference engine and a rule base. The rule base contains the knowledge about the domain in which the program is to operate. The inference engine is a sort of driver that knows how and when to invoke these rules. The main advantages of this technique are:

- it keeps the code small because the generic part is written only once instead of being embedded several times in the application specific parts. Enhancements to the generic part automatically benefit all specific parts;
- the knowledge is isolated from the solution-generating procedures. If something changes in the specifications of the problem only some rules will have to be added, deleted or updated. The application program code is not obfuscated by general program code and vice versa. Usually the rules (or groups of rules) can be reviewed independently from each other. This makes the program easier to maintain because the program lines that need to be changed to cater for an adaptation can more easily be identified and isolated. Due to this isolation, errors made in rules tend to have only local effects: usually the other rules can still be used correctly and erratical behaviour is contained to a small part of the program;
- there is an implicit standardization since the generic part ("the inference engine") determines the structure of the rules. This standardizes the structure of all the application specific parts defined using those rules.

Since a Prolog program is itself a rule base, this technique comes very natural in Prolog. This design is taken a step further. When the knowledge can be split into several layers, one can reflect these layers in the program's design. The inference engine drives the use of a high level set of rules and some of these rules trigger the use of lower level rules. This allows minor changes to be performed at the lowest level of rules without having to changing the intermediary level of rules. Again the advantage is further partitioning of the program code and thus ease of maintenance.

This technique is analogous to what is called "data driven programming" in sequential programming languages. In Prolog, a program has the same structure as data. So the "data" that drive the program, can be programs themselves. This gives the leverage in software engineering needed for large systems.

Building Custom Interpreters

Another advantage of the similarity between data and programs is that one can manipulate Prolog programs the same way as Prolog data. Advantage is taken of this feature of Prolog to build the own limited interpreters.

Often the same type of program code needs to be written repeatedly during a project. If one can pinpoint the differences between these programs, it was found to be more cost effective to create a sort of special purpose "language" specific to the problem, and write an interpreter for it. The interpreter reads the program instructions in the new language and translates them.

This technique is used in a simple form. The "languages" created adhere to the Prolog syntax and thus can be represented by Prolog data structures. This made the manipulation of these structures by the interpreter trivial. Often this structure contained a list of high level commands to be executed. The interpreter reads this structure and selects the Prolog rules to trigger based on the information in the structure.

The advantage is that only the relevant parts of the code need to be written (the rest is generated). The program is shorter and easier to maintain. The disadvantage is that an interpreter needed to be written, but in Prolog this is much easier than in other languages. The point where the cost of writing the interpreter is offset by the gain of the automatic creation of program code is reached faster when using Prolog than when working with more conventional languages.

The Architecture of the data model according to the invention has several levels of data models which can be grouped into a meta-model (see FIG. 1). There are four different parts to the overall data model. Three of these are built one on top of the other and the fourth (the non-conceptual tables) is a parallel model that is used at all three levels. Structuring the relationship between these data model levels facilitates the reasoning about data during development. As described later on, most of the programs manipulate data at only one level of the data model. Each of these data models and their relationship to each other will be discussed, and finally, the use of the non-conceptual tables in optimizing performance will be demonstrated.

Physical Data Model

As mentioned above, the content of a form is a message. The physical model deals with the storage of these messages. Apart from the application defined fields, for each message a set of standard fields (a.o. who inserted the message and when) is added. These fields are also used to implement the support for the deletionless aspect of this level. This level is deletionless since no information is ever destroyed.

Whenever a user deletes a message, it is not physically deleted but only marked as deleted. The system also stores who deleted it and when. Whenever a message is updated (corrected), the update is translated in an insert of the new message and a delete of the old version. The system stores who inserted the new version and when, and links the new version to the old one. FIG. 2 shows the standard fields needed to implement this data model. In every system conceptual table these fields precede the application specific fields. The function of each of those fields will be briefly described, and then it will be shown how they are used. A unique number for each (version of) a message in a table. The dkey plus the table name uniquely define a message.

The dkey is assigned by the system at insert time. The dkey and the sender are displayed in the right hand corner of the form to confirm the acceptance of the message by the database.

omit is one character with three possible values:

i: inserted: this is always the first value for this field o: the message was omitted (logically deleted)

c: the message was corrected by another message.

sender and sendTime username value of the person who sent the message and a timestamp value.

omitter and omitTime

These are initially null and will only get a value whenever the message is deleted. In that case they will contain the username of the person deleting the message and the time of deletion. At that time the omit field will be changed from 'i' to 'c'.

cdkey

Is only used if a message is a correction for a previous message. In this case this field will hold the dkey of the corrected message. This field "links" the new message to the old message.

EXAMPLE

Suppose we have a table containing messages with only one application deed field called X. There are already two records in the table. One with the application content AAA and another with the application content BBB.

| dkey | omit | sender | sendTime | omitter | omitTime | cdkey | X |
|---|---|---|---|---|---|---|---|
| 1 | i | Jeff | 21.7.95 15:03:04 | | | | AAA |
| 2 | i | Ann | 22.7.95 09:33:12 | | | | BBB |

If Jeff now omits the message sent by Ann the table will become:

| dkey | omit | sender | sendTime | omitter | omitTime | cdkey | X |
|---|---|---|---|---|---|---|---|
| 1 | i | Jeff | 21.7.95 15:03:04 | | | | AAA |
| 2 | o | Ann | 22.7.95 09:33:12 | Jeff | 22.7.95 09:35:14 | | BBB |

If Ann corrects the message that was sent by Jeff (and changes the content from AA to CCC, this update will be translated in an omit of the original message and an insert of the new message.

| dkey | omit | sender | sendTime | omitter | omitTime | cdkey | X |
|---|---|---|---|---|---|---|---|
| 1 | c | Jeff | 21.7.95 15:03:04 | Ann | 23.7.95 11:12:13 | | AAA |
| 2 | o | Ann | 22.7.95 09:33:12 | Jeff | 22.7.95 09:35:14 | | BBB |
| 3 | i | Ann | 23.7.95 11:12:13 | | | 1 | CCC |

The actual insertion of the username, timestamp, etc. in the System header fields is not directly done by the application programs but is accomplished using "triggers". The three basic operations (insert, omit and correct) can easily be initiated in a standard way from each electronic form. The electronic forms in the present system all share a standard header of icons. Each of the functions is linked to an icon in the header. The formTools module of the present system generator handles the processing of these functions for all forms in a generic way.

Due to the deletionless-ness, the physical level contains also a log of all versions of all messages. This has several advantages. The first is that whenever there is an argument as to what information was available at a certain point in time, the state of a message or group of messages that time can easily be reconstructed. Although only the programmers can query the physical level to retrieve previous versions of a message, some privileged users (the administrators) can retrieve a history of the versions of a message. This history lists who changed a message and when. If a user has questions about the version history of a message, the administrators can give him the names of the people involved. If necessary, the actual versions can also be retrieved and compared.

The second and most important advantage is that every user is responsible for every bit of information he enters into the database. This is also the reason why the dkey and the sender's name are shown when a form is sent: it reminds the user of the fact that the database has accepted the message and stamped with his name. The unique number identifies this version and any subsequent updates can never erase this version. When changing or overwriting information in a written medical file, it can almost always be seen that some information was overwritten. In a computer this is not the case. The new version of a medical report looks as pristine as the previous one. This lowers the resistance to change information in an electronic medical record. The aim of the logging of all changes and the constant reminding to the users of this logging is to compensate for the lack of visual traces of the overwriting.

Conceptual Data Model of the Generator

The basic layers of the present system software are called the generator. In the conceptual data model of the generator, the deleted messages and older versions are logically omitted from the tables. A table at this level contains only the last version of each message. This level is used in all application queries and the physical level is completely hidden (except for the version history query for administrators).

This level can easily be created by defining relational database views on top of the x# tables. By convention, the name of this view is the same as the underlying table but without the x# prefix. The definition of the view foo on top of x#foo is shown in FIG. 3. The structure of these views are simple, thus they do not hamper performance. To all intents and practical purposes this view behaves as the conceptual base table for all higher level data models. Therefore these tables are called table-views.

Updates and deletions of messages should only be used in case of errors. This is only possible if the application data model is an additive model. This implies that a message should contain information all of which is known at the expected time of data entry by a single user. The user must be able to send all the information as a whole to the database. E.g. if two information items A and B are not known at the same time, but operational procedures require the data entry of item A into the system, then item B cannot be part of the same message (and part of the same electronic form) as item A. If it would, the procedure would force the user to guess the value of item B (or to leave it blank) when sending the message. When item B becomes known, the user would then have to correct the message. Such a situation is considered a data modelling error for an additive data model. Again compromises have to be made to keep the system ergonomic. Taken to the extreme every data item could be a different message. This would avoid the problem above since one never has to send two or more items on one form. In an ideal world with infallible and omniscient users the content of this level should exactly be the same as the content of the physical level.

Conceptual Data Model of the Application

This level is based on the conceptual model of the generator. This level defines the fields that hold the contents of the messages. An application data model defines an information stream. Each user (or function generating information) is localized somewhere on this stream. A user receives the messages from the people upstream and adds his information using electronic forms for the use of the persons downstream. This is exactly the same as with paper forms. A paper form is completed and then sent to the next person in the information stream. This person will probably generate new information and send it (back) to the next person in the stream.

This data modelling strategy allows the users to take on a more active role in defining the data model. Usually the future are asked users to think as if they will re-engineer their procedures using paper forms. There are a few extra assumptions they are allowed to make because of the electronic nature of the forms:

the forms arrive at their destination virtually immediately;
a form can be viewed by several persons at the same time (there is no serialization necessary if two persons need the same information);
parts of forms can be hidden for some (types of) users.

The users can build their data model together with the analysts, so they understand what the data model represents. This transparency allows them to deduce which information functions are possible and which ones are excluded by the data model. This contrasts with the more classical approach where the analyst extracts the specifications for the different functions that need to be accomplished by the information processing system, and subsequently builds a data model to support these functions. When the user changes the specifications or when new functions need to be added, it is possible that these do not fit well onto the data model. The data model then needs to be adapted, which is costly. By taking on a more transparent approach towards data modelling the user can guard compliance of the data model with his world view.

Benyon states that a data processing model is built from a data model and a process model. The data model represents the structure of the enterprise by modelling it in terms of objects and relationships between those objects. The process model focuses on the transformations which take place in the system. These processes transform the data through some manipulation, re-structure it more usefully, or relate it to other data. The data model and the process model respectively represent the static and dynamic features of the information model.

Mapping one's data modelling technique on this type of data modelling, one could say that the process model is highly simplified. Processes in the real world result in only one type of change in the database: the addition of a message. No data are manipulated or restructured by any user originated function. This simplification adds to the transparency of the data model. As stated before, this simplification in data entry and manipulation leads to more complex deductions. So the price to pay is performance. This is solved by trading deduction performance for storage space and insertion performance as explained in the next section.

Non-conceptual Tables (Application Level) Optimize Performance

The message modelling technique treats a business process as a flow of messages. The status of a business process can be deduced from the presence and absence of messages. As an example, 5 of the messages involved in an outpatient visit are examined. A reception form is filled when the patient arrives (1). Then the patient is assigned to an assistant and a supervisor (2). The assistant will write a report after the visit (3) and the supervisor will validate this report (4). The secretary mails the report to the (external) doctor who requested the examination (5).

Each of these messages can be sent by a different person. The messages have to be sent in this sequence. It is obvious that one cannot validate a report that does not exist but the system will also check that a report cannot be written if the patient is not assigned to an assistant and a supervisor. For each outpatient visit all four forms have to be completed (allowing a number of exceptions). The five phases describe a unit of work.

The status of this unit of work called "ambulatory care visit" is the progress through these five phases. The phase the patient is in, and the next step to do, can be deduced from the presence and absence of the messages. This way the system will make worklists to show the users the specific information necessary to accomplish their work. E.g. the assistants will want a list of all patients that have been receptioned but not yet assigned. They will start from this list to divide the work among them. After assigning patients (sending the electronic assignment form) they will see and treat the patient. Later the assistant uses a list of all patients assigned to him but for whom no report is written yet, to start writing the medical reports. The supervisor will want a list of all unvalidated reports for patients assigned to him.

Each of these work lists is defined as a view in the relational database 101. The structures of these views are similar: they select patients for which a particular message exists and another message does not exist. Only a small part of the tuples in each of the tables will participate in these queries, namely the tuples pertaining to units of work for which not all five phases have been completed. These units of work 111 are said to be in production. Most of the data will be on units of work 103 not in production: data about visits that have validated reports.

For the work lists mentioned above most of the computational work is of the type "find tuples from table A for which there isn't a tuple in table B". For real life queries obviously more than two tables will participate in the query. The performance of the query will deteriorate as the size of the tables grows. In a medical setting historical data are so important the users want to keep information on-line as long as possible. This means that as the database grows performance will degrade. Two types of tables can be discerned: static and dynamic tables. Dynamic tables 105 grow in size at approximately the same rate as units of work are added to the database. E.g. the report table is a dynamic table 105: for each visit of the patient to the hospital one or more reports will be written. Static tables grow at a much slower rate, which is usually not linked to the amount of units of work 103. E.g. a table of definitions of radiological examinations will grow as more techniques for medical imaging or new machinery becomes available. Other examples are the tables containing doctor identifications, ward numbers and descriptions, medication lists, . . . These tables also grow, but several orders of magnitude slower than the dynamic tables. They usually contain hundreds or a few thousand records.

Queries (like work lists) used to support the normal workflow are called production queries to discern them from management queries. Production queries need fast response times to assure a smooth workflow. Production queries can be divided in point queries and set queries.

Point queries are queries that give all tuples pertaining to one known entity and has an indexed identifier. E.g. all reports for a single patient; or all assignment forms for a single supervisor. Set queries range over several entities and are usually of the work list type as described above. Point queries can be speeded up using indexes that are available in any commercial database system. Set queries also benefit from indexes but these are not sufficient to reach the required performance level. The solution found for this problem was using extra tables to store the information needed to speed up these queries. These tables contain only redundant information and do not exist from a conceptual point of view. Hence the name non-conceptual-tables 109. Status tables are non-conceptual tables 109 containing information about the status of a unit of work. The non-conceptual tables 109 make up an alternative redundant data model. It is a compressed data model since only the redundant information needed to speed up the selection of the relevant units of work needed in queries is stored. In a way the non-conceptual tables 109 act as semantic indexes to the data in the conceptual tables. Once the relevant units of work are identified the actual data are retrieved from the conceptual tables.

To optimize the ambulatory care example, a status table should be needed with four attributes in addition to the four tables containing the messages for the reception, assignation, report and validation form. In this status table visitID contains the identification number of the visit, assigned contains 0 or 1 indicating the existence of an assignation form for this visit. Report also contains 0 or 1 indicating the existence of a medical report. Whenever a new unit of work starts, a record is created in the status table (see FIG. 4*a*).

The tuple above indicates that a visit with identification number 7 is in production and that only the reception phase has been completed. When the visit is assigned to an assistant and a supervisor, the assigned bit is flipped from 0 to 1 (see FIG. 4*b*).

When the medical report is sent to the database the report bit is flipped. When the report is validated the next bit is flipped. When the "sent" message is added to the database the record for that visit is deleted from the status table. Sending is the last phase so the unit of work is no longer in production. The status table (non-conceptual table 109) contains information on all visits:

all visits not represented in the table are out of production; the visits that are in production can be in either of four states receptioned only receptioned and assigned receptioned, assigned and reported upon receptioned, assigned, reported upon and validated (i.e. no status record is present).

Time is also represented differently. In the non-conceptual tables 109 time progress is represented in the columns: as work for a unit of work progresses, values in the columns are updated. In the conceptual tables 105, time progress is represented in the rows. Completing a phase in a unit of work 103 means adding a rows to a table (see FIG. 5).

The status table (non-conceptual table 109) allows to rewrite queries that test for the existence of messages and make them more efficient. Assume that all visitIDs and patient names of visits that still needed to be validated by supervisor A are wanted. Without the status table this means going through the "assigned" table and for each visitID assigned to supervisor A go through the report table and check for the existence of a report with the same visitID. For each of those reports, check in the validation table whether they are already validated or not. For those for which no validation tuple exists, retrieve the patient name from the reception table.

Both the "assigned" table and the report table are dynamic tables. Most of the records in the assigned table have validated reports since only a limited set of all data will be in production. So the existence test for a record in the validation table will most of the time find that the report is already validated.

The same query is much faster to compute using the status table (non-conceptual table 109). Since it is very much smaller, it allows to find the units of work 111 that are still in production much faster. This will be shown in the following experiment which is part of the query that supervisors use to retrieve the list of reports they have to validate.

Experimental Proof of Performance Gain

As an example (a part of) the query to retrieve the validation list for a supervisor in the clinical workstation is shown. The query retrieves the list of reports that need to be validated by the supervisor assigned to handle that unit of work (i.e. a patient contact).

In the case of the supervisor used in the example, the query returns 6 rows (i.e. 6 reports need to be validated).

Six conceptual tables take part in this query. A short description of these is given in Table 1. In an experiment, 3 versions of the same query were shown and their performances were compared. The first version is a straight declarative implementation of the query. The second version uses the non-conceptual tables to enhance performance. The third version does not use the non-conceptual tables but is written more procedurally to help out the optimizer.

To compare performance, the time spent in evaluating the query and the number of times each table was scanned to find the solution were measured. The query optimizer can choose to access a table more than once because it does not find it optimal to do all data retrieval in one access. Usually the table will be scanned several times during one access. Sybase allows to print out the order of accesses (the query plan) but it does not tell which data where retrieved in each access.

The Version

The first version does not use the non-conceptual tables. The query is written as one declarative select statement and all optimization is left to the query optimizer (see FIG. 6). The query optimizer only has syntactic information and thus does not "know" that most of the reports in the report table will be validated ones. The order of accesses and the use of an index in the access is listed in Table 2. The complete query plans for all three queries are listed in Table 3. From the order of accesses, it can be seen that the server chose a path in which it needs to access the x#verslag en x#validatie tables several times before it has identified the units of work that are relevant. Once these are identified, it accesses the other tables to retrieve the attributes that need to be displayed.

In Table 4 the performance results are listed. Query 1 took 129 seconds to complete. Most of the time was spent in scanning the x#validatie table to resolve the "not exists" test in the subquery.

Version 2

The second version of the query uses the status table and is listed in FIG. 7. The status table not only stores flags to indicate which phases have been completed but also the identification of the supervisor and the assistant to whom the unit of work is assigned. This means that both the selection based on the supervisor and the selection based on the existence of a validation can be done simultaneously on the status table. The name of the patient is also stored (redundantly) in this non-conceptual table since almost all production type queries need to show patient names.

As in query 1, this version is written as a single select statement and all optimization is left to the optimizer. An optimizer always tries to reduce the number of tuples to be processed as early as possible in the query. The optimizer has no problem identifying the optimal path for this query. It has three selection criteria (s.usernameSup="x163646", s.verslag=1 and s.validatie=0) on the statusContact table which also happens to be the shortest table. From this information it surmises that the biggest reduction in tuples to be processed can be gained from accessing this table first.

This results in dramatic speed increase (elapsed time less than 0.5 sec). As can be seen from the query plan in the appendix, the query now accesses first the statusContact table using the index on supervisor, immediately identifies the 6 units of work that are relevant and accesses the x#S9User and x#verslag table to retrieve additional attributes not present in the status table. The number of table scans is thus greatly reduced.

The problem with query 1, is that the optimizer builds a non-optimal plan. Its heuristics can only use information from the structure of the query, the length of the tables and the presence or absence of indexes. It cannot use the semantic information that the application programmer has. In the case of query 1, the optimizer takes the wrong decisions and becomes a "pessimizer". In such cases an application programmer can increase the performance by enforcing a more optimal execution order. This is usually done by splitting the query in parts. The query optimizer will still optimize each of these parts but cannot change their execution order. Some of the advantages of SQL are lost this way. The query is harder to read, takes longer to write and if the length of some of the tables changes fundamentally, the optimization has to be redone. Nevertheless, this technique is often unavoidable for very complex queries.

Version 3

The third version of the query does not use the status table but is optimized by splitting it in three parts (see FIG. 8). The first part creates a table containing the identifiers for the units of work assigned to the supervisor. In the second part, all tuples pertaining to units of work that are already validated are deleted from this table. With the resulting identifiers, the other tables are accessed to retrieve the attributes that need to be displayed. This sequencing of the computation is imposed because it is known that only a small percentage of the reports needs to be validated. Because semantic information is used (which is unknown to the query optimizer), this optimization technique is called semantic optimization.

This query is much faster than query 1 but still more than 7 times slower than the query using the status table. Although the number of scans has been dramatically reduced, the first two parts of the query that identify the relevant units of work have more processing to do than using the status table: the x#validatie table needs to be scanned for all reports that are assigned to supervisor "x163464".

Query 2 is by far the fastest query especially if one looks at the CPU time. In query 1 CPU time nearly equals elapsed time. This means that the query is CPU bound: the CPU is the bottleneck. Query 2 needs less than 100 ms CPU time (Sybase reports CPU time in units of 100 msec) so most of the 446 msec is spent waiting for disk access. The actual processing is very light. Query 3 is situated in between. Apart from the performance advantage, query 2 also is much more readable than query 3.

As the number of units of work in the database increases, the performance of query 1 and 3 will deteriorate since both of them need to scan tables that grow with the number of units of work. Query 2 scans the statusContact table. This table will remain in a steady state if the workload on the department does not change fundamentally. The number of accesses to other tables does not depend on the total number of units of work in the database but on the workload of the supervisor which will also be in steady state. The actual accesses to these tables are indexed accesses and thus only deteriorate logarithmically with the response time.

Using non-conceptual tables is trading in insert time and disk space for shorter query time. The redundant tables are kept up to date and synchronized with the conceptual tables using database triggers. Inserts become slightly less performant because at insertion time redundant data have to be updated or added in the non-conceptual tables. This is analogous to indexes. These also contain redundant data, and adding indexes to a table slows down insertions but speeds up queries. Because triggers are used to maintain the non-conceptual tables no extra overhead is placed on the application or on the network traffic between the client and the server. All overhead is on the database server.

At the start of a unit of work (e.g. the reception form in the experiment above) the insert in the reception table also causes an insert in the status tables. All subsequent phases in the unit of work cause updating one or more fields in the corresponding record in the status table. Usually an insert causes numerous checks to be done by the database server. E.g. when an assignment is made to an assistant and a supervisor, the system will check if the identifications in the assignment form exist in the identification table for MD's. If one orders a radiological examination, the system will check if this type of examination exists. Often several of these types of checks will take place during the insert process. Usually an insert takes a few milliseconds so the additional overhead of maintaining the non-conceptual tables is negligible for the end users.

The other price to pay is disk space. The overhead here is low (see Table 4) and decreases as the database grows because the ratio of units of work in production versus historical units of work decreases. The number of records on a status table remains relatively constant when the department is in a steady state, that is it finishes as many units of work as it starts. There may be some fluctuations in the number of units in production (seasonal changes, shortage of personnel, . . . ) but eventually a steady state has to be reached.

What is gained is query response time as illustrated in the example above. Since a message is inserted once but queried many times the benefits clearly outweigh the costs.

A relational database not only optimizes the query paths but also memory management. Often used data are kept in main memory because the server anticipates that they will be used again and wants to avoid the overhead of disk access to retrieve them. Since most of the production queries use the status tables and most of the users use (only) production queries in their daily routine, the status tables are constantly accessed. Because they are small they can reside completely in memory. This has an additional positive effect on query response times because most of the accesses to the status table will only be logical reads (only in internal memory) and no physical reads (disk access).

In conclusion there are 3 reasons to keep the status tables small:

the less redundant data there is, the less synchronizing needs to be done at insertion time.

the smaller the status table, the more chance there is it will stay memory resident.

use of disk space.

At current disk storage prices the third reason hardly plays a role anymore. The first two have to be offset by the gains in query performance.

Separating Design for Performance from Design for Expressivity

Maybe the biggest advantage of using non-conceptual tables is that less compromises need to be made in the conceptual data model to ensure performance. In the present methodology, the design for representation and the design for performance are split over different data models. This gives much more freedom in the representational aspects of the data model. The conceptual tables are externally visible through the functions in the system. The non-conceptual tables are invisible to the users. If in time the query patterns change and other functions need to be optimized, non-conceptual tables can be added or changed easily and then rewrite the queries to be optimized to use these tables. The data model as the users see it, remains unchanged.

Recovery Time

The non-conceptual tables allow the database to grow while query performance degrades only with the logarithm of the database size. This removes one bottleneck to unlimited database growth. The next bottleneck that will arise will be recovery time. The larger the database, the longer it takes for back up or to reload it from tape in case of media failure. Although this is a much less stringent constraint on database growth, it cannot be ignored. For each of the databases, it must be determined which is the maximum recovery time allowed. This, in combination with the maximum backup- and-restore bandwidth, will determine the maximum size of the database.

Effect on Database Size

The amount of corrected or omitted messages varies greatly from table to table. E.g. the assignment form for patients on a ward is corrected each time the physicians are assigned to new wards. The reports table contains many logically deleted reports since even a minor correction like for a typing error causes a copy of the report to be saved. All overhead in other tables is dwarfed by the overhead in the reports table: not only is this the table with the highest number of corrections, it is also the table with the biggest rows. Each report text field takes up at least 2 kilobytes Architecture Where the clinical workstation is used in direct support of the clinical work, X-terminals are preferred for their robustness. On private desks or for secretaries a personal computer is more suitable. Robustness is less of a problem here. These machines are usually less critical to the operation of a department than e.g. the clinical workstation in an operating theatre or a nursing ward.

Hardware Architecture

Conceptual Network Architecture

Figure 9:
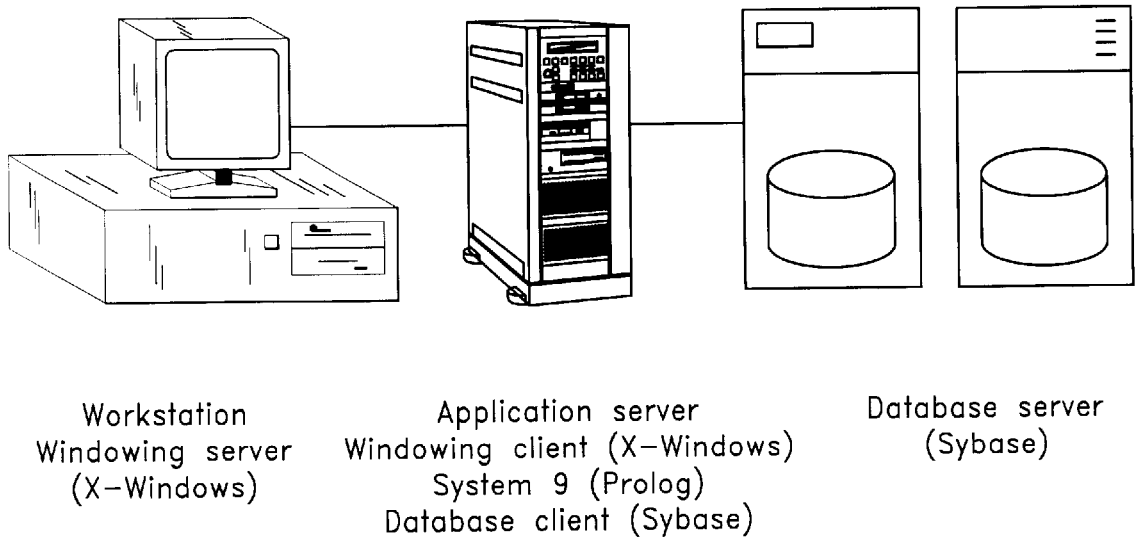
FIG. 9 is an illustration of a conceptual hardware architecture of the system consisting of three tiers.

The conceptual hardware architecture of the present System consists of three layers: a presentation workstation, an application server and a database server. These are connected by a network and act as a single system (see FIG. 9). For each of the three conceptual tiers different physical machines are used. This allows to choose a hardware configuration for each tier that is optimally tailored to its function.

Presentation Workstation

The presentation workstation only runs the presentation software and holds no application logic. No "programming" is done on this machine. This is the machine on the desktop with which the user interacts. The system needs to be capable of running a graphical user interface but should be controlled by programs on the application server. For the first two implementations of present System (Surgical Pathology and Radiology) Macintoshes where chosen as presentation workstations. The Macintosh was at that time (1990 and 1992) the most cost effective system capable of running a graphical user interface: it had a graphical operating system, networking was built in and it was easy to administrate.

As already mentioned, X-windows was chosen as the user interface software for the clinical workstation. This software can be run on PC's, Macintoshes or specific hardware called X-terminals. These are "intelligent" terminals capable of running a graphical user interface but without the need to store local software. X-terminals look like workstations. They have a processor and internal memory but no hard disk. When an X-terminal is started up ("booted"), it connects to a host computer which uploads all the necessary software. This is the reason why no local hard disk is needed. They are also easier to administer since, after installation, hardly any local interventions are needed. The X-terminal has a local processor and memory but this is only used for the processing and data storage needed for the presentation software. The absence of a hard disk and lack of local software makes the X-terminal much more robust than a personal computer. These machines rarely crash since they have no moving parts. If they crash they can be swapped for a similar model without much effort since no local files need to be transferred from the old machine to the new one. The cost of client-server solutions is much higher if one works with personal computers as compared to X-terminals. By '93 the cost of an X-terminal was higher than that of a Macintosh, but the difference was so small that it was offset by the cost of migration halfway through the project.

While the X-terminal lacks the disadvantages of a PC, it also lacks the advantages of the PC. No local processing is possible and the standard office automation packages that are widely available on personal, computers have no real counterparts on the UNIX machines that usually acts as hosts to the X-terminals. The X-windows software that runs on the X-terminals, can also be run on personal computers. In those places where one workstation is used both as a front-end to the hospital information system and for office automation, a Macintosh is placed with X-windows software. Since the application server converses with the presentation software via the X-windows protocol, no additional programming needs to be done on the application server to support this configuration.

Application Server

The application server runs the present System environment. All application programming (with the exception of stored procedures, views and triggers) is done on this system. The application server controls the presentation workstation via the X-windows client software and is a client to the database server. Only transient data that are not shared by multiple users is stored on this system. This allows to have many application servers because each can function independently from the others: all data that need to been seen by other users is sent to the database server and all application servers are connected to it.

The application server executes CPU intensive tasks. Events from the windowing server trigger some Prolog programs. This results in issuing commands to the windowing server. Sometimes data from the database server will be retrieved. But no large amounts of data are processed on the application server. The disks on this machine are only needed to store the operating system (and other software necessary to exploit the machine), the programs for the clinical workstation and swap space. Each Prolog process requires on average 22 Mb of virtual memory. The ratio of physical memory over virtual memory is influenced by the expected number simultaneously active users and the number of functions in the application. The more functions in the application, the smaller the procentual part of the program that will constantly be used: a user can only do a few things simultaneously. Since each user has a specific task, he or she will only (repetitively) use and keep using a subset of all possible functions. This is called locality of function. A receptionist will fill in reception forms and continue to do so for most of the time. Due to locality of function the part of the program that is needed in physical memory (the resident set) will not change during the use of the application by the same user.

Database Server

The database server runs only the server part of the database. On this machine all data that are shared between users is stored. There is only one database server for all application servers. The database server receives SQL commands from the.applications via the Sybase client software. No System programs run on this machine but some application knowledge resides on this system in the form of database triggers (used for consistency) and procedures (mainly used for reporting).

By using a separate machine as database server, its configuration can be tailored optimally to its use. The database server handles large amounts of data so this machine needs to be able to handle large volumes of disks. Most manufactures have machines in their product lines that are specifically geared towards database operations.

Example of the Processing of an Event in this Three Tier Architecture

Figure 10:
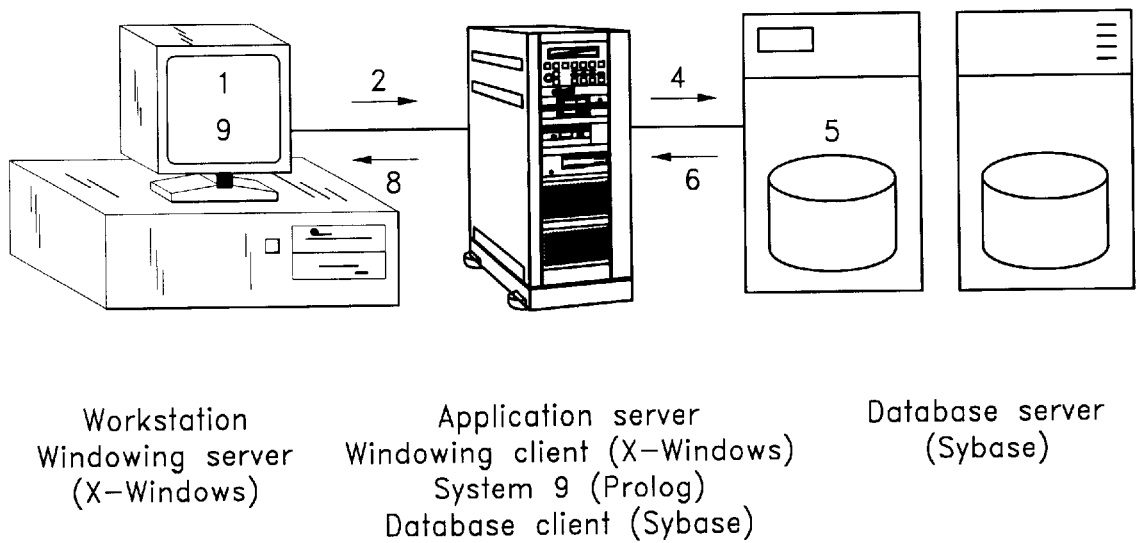
FIG. 10 is an illustration of a processing of an event.

Suppose a user presses a button on a dashboard to retrieve the medical report linked to a particular hospital stay (see FIG. 10). When the user presses the button (1), the X-windows server detects this event. (2) The windowing server notifies—via the network—the windowing client on the application server of the event. The client triggers the execution of the program written to handle this event. (3) The program will prepare an SQL statement to retrieve the report. (4) A Sybase client function is used to send the SQL—again via the network—to the Sybase database server. (5) The database server executes the SQL statement, retrieves the data from the database and (6) sends them to the client. (7) The present System program on the application server uses several Sybase client functions to read out the data. (8) Using X-windows client functions, it creates a report window on the X-terminal (via the network) and (9) displays the data using this report window.

Physical Network Architecture

In reality, the three types of computer are not connected to each other serially. The physical network architecture uses a backbone Ethernet network to which the application servers and the database server are connected. These reside in the Main Equipment Rooms (MER). From the MER fiber optic links are made to Satellite Equipment Rooms (SER). This is called the "vertical" cabling. A SER is a small room containing a patch panel. Each network outlet is connected point-to-point to the patch panel in a nearby SER. This is called the "horizontal" cabling. A universal cabling system is used for this connection. By making minor changes at the outlet and placing the appropriate active components in the SER, these cables could be used to support the most common network and terminal protocols (Ethernet, token ring, AppleTalk, RS 232, IBM 3270, . . . ). The active components in the SER are connected via vertical cabling to the servers in the MER.

The main advantage of this cabling system is that a building can be cabled when it is constructed. It is not necessary to know the type of network connections in advance. Also, no cables have to be replaced if network services need to be changed for a particular room. E.g. if a user changes from a terminal to a PC or X-terminal, his network outlet needs to be reconnected in the SER to another active component. Possibly the external plug needs to be changed. The cabling needs no changes.

Upgrading the network to handle higher throughput (e.g. switched Ethernet or ATM) will be done the same way. The disadvantage is that to keep the system universal some constraints have to be taken into account. The distance between the SER and the network outlet cannot exceed 100 meters and has to be a point-to-point connection. This means that enough network connections need to be foreseen for each room since it is not possible to connect a workstation via another workstation.

The Scaling of the Present System

Since present System will take a few years to install hospital wide, the system will need to be scaled during that time. The effect of scaling on the three tiers of hardware will be examined. Three dimensions of scaling are considered:
the number of users,
the size of the application (as the number of functions grows, the amount of program code will grow also), and
the amount of data stored.

It will now be investigated what needs to be done on each of the hardware levels to accommodate the growth in each of these dimensions.

Presentation Workstation

This is the easiest level to scale: one is added per workplace. The amount of data in the database does not influence the parameters of this workstation because the user will always require lists of a length that can be read on screen. It is no use to let the report lists grow as the amount of data in the database grows.

The same holds for the size of the application. While the number of windows that can be opened might grow, the number of windows simultaneously opened by a user is limited by what is ergonomically acceptable. If too many windows clutter the desktop, the user will close them automatically.

For a given a type of function, adding more functions will not require a more advanced workstation since the user is the limiting factor and he will only use a small subset of this larger whole simultaneously.

Application Server

The application server also scales trivially with the number of users: each type of application server can accommodate a certain amount of users depending on its processing power and internal memory. Adding users means adding or expanding application servers.

If the size of the application grows, more virtual memory will be needed per user since more program code and more data structures need to be stored in memory. Either more memory is added or more application servers are installed (adding both memory and CPU capacity).

The amount of data stored does not influence the application server since these only pass through the application server which formats them to be displayed on the presentation workstation. Since the data are not stored and the number of records will automatically be limited by what can still be handled by the users, the amount of data that needs to be processed by the application server will not increase with the length of the database.

Database Server

The database server needs to be scaled with the number of users: more users means more simultaneous queries and transactions. Both memory and processing power will need to be added. Database servers do not scale linearly by simply adding hardware.

The size of the application alone does not influence the load on the database server: the users will have more ways to view the same data. This might result in more usage of the computer but, since a user can only do one thing at a time, this increase will not be significant.

If the amount of data increases significantly, more disks need to be added and probably more processing power and memory (if the response times of the queries are to be kept constant). The query performance scales logarithmically with the size of the tables due to the present data modelling technique. The data modelling technique does not solve the problem of multiple users simultaneously doing updates in the database. More users and more data need to be offset by adding hardware and smarter database algorithms.

It is expected to have at the most 1000 concurrent users in the present System. This can be handled already by current technology. Database vendors are improving the parallellization of their servers and computers with 10 and more processors are state of the art. Therefore it is possible to scale a database to more than 1000 users.

In conclusion, scaling the present System comes down to scaling the back-end database server. All other levels scale linearly by adding hardware.

Software Architecture

To separately develop applications for all departments in the hospital would require too much resources. The implementation time for the whole of the hospital would be unacceptably long. In order to speed up development, it is decided to develop a set of generic software modules first to serve as larger building blocks for subsequent applications. The software developed at the U.Z. Leuven can be divided in 4 groups: the System generator, the System tools, the builders and the clinical workstation modules. The Surgical Pathology, Radiology and clinical workstation modules all share the generator and System tools as basic building blocks.

The first three types of modules are generic modules and will be discussed here.

The System Generator

The System generator consists of three modules that closely interact with each other. It provides a higher level interface to Sybase and X-windows and implements the concept of forms on top of a deletionless database in a generic way. The generator is not specific to hospitals.

Figure 11:
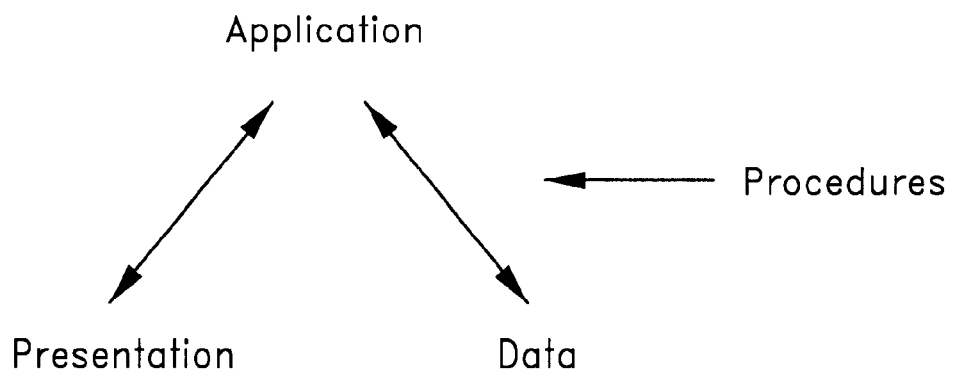
FIG. 11 is an illustration of an application which can be viewed as a device that sends data between a database management system and a presentation layer.

In FIG. 11, is represented the data ship between presentation and database. In an application, data are constantly shipped between the screen (the front-end, in the present case X-windows) and the database (the back-end, in the present case Sybase). In between, formatting, manipulation and checking of the data is done by the application. Procedures are specially structured application parts used solely for checking data integrity. The generator provides tools to do much of this shipping between front-end and back-end.

Because of the use of the form metaphor, all parts of the application related with forms can be handled in a generic way. The three modules are:

motifShell,
messageTools and
formTools.

Figure 12:
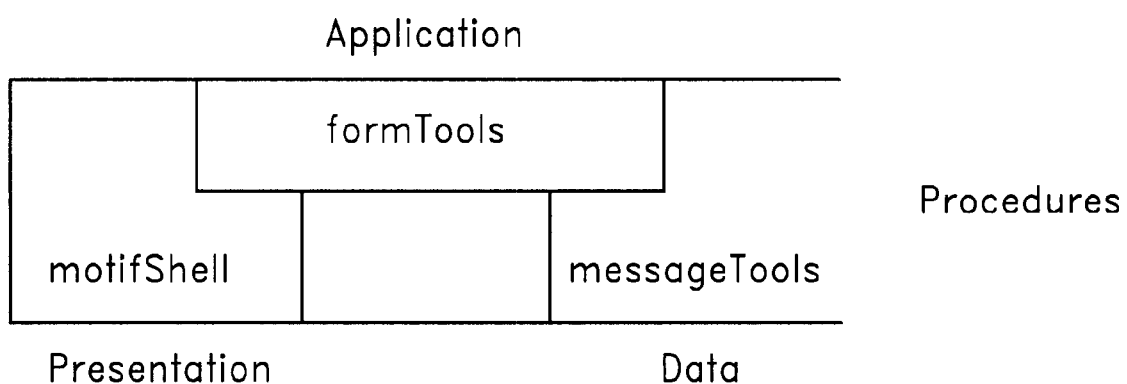
FIG. 12 is an illustration of the system generator consisting of three basic modules.

Their interaction is shown in FIG. 12. Modules can use lower modules but not vice versa. E.g. the application can use formTools, which in turn uses motifShell, which uses X-windows to display data on the screen, but motifShell can never call functions from formTools.

MotifShell

MotifShell is used to handle all presentation tasks in the present System applications. Roughly the module serves three purposes:

a Prolog interface to Motif/X-windows,
implementation of high-level interface objects, and
speed-optimization.

By having a generic module to handle these tasks, it is avoided having to redo this for every program or application, and the access to the X-windows presentation package can be standardized, thus facilitating maintenance.

Prolog Interface

The first purpose of this module is to shield the System programmer from the low level details of X-windows. All X-client functions have their Prolog counterparts and these are used in application programming. It is the Prolog version of the X-windows client software. Apart from this low level functionality, motifShell provides powerful high level predicates that automate part of the work of creating and managing windows in X-windows.

The creation function of the window is generated by a tool called Builder Xcessory (BX). This tool is used only to design the window ("paint"). Only the resources needed to determine the type of widgets and their positional interactions (alignment to each other, determining which widgets manage other widgets) are set using BX. These are resources that are relatively fixed in time and that will need little maintenance. All resources that will probably need maintenance in the future are set in the Prolog application. This allows to generate the creation function with BX, link it to the System application and almost never touch it anymore. All maintenance can be done on the Prolog level.

To speed up application development, a small interpreter was constructed to allow the setting of resources on a higher conceptual level. For each type of window ("shell") a data structure must be defined. This data structure contains high-level instructions to set or modify window parameters (see FIG. 13). A small program reads these and for each instruction there are one or more rules determining what low-level instructions need to be executed. One instruction can result in the execution of several low-level X-windows client instructions. Prolog is very apt to write these types of programs. Having such an interpreter speeds up application development because many complex tasks can be bundled in one System instruction. The interpreter is easy to maintain because the program that drives the execution of the high level instructions, uses a rule base to "decode" them. To add high level instructions, only add rules are needed. These rules can be maintained independently of each other.

High Level Display Items

MotifShell also defines very high level "widgets" such as the logicBox. The logicBox is a widget that maintains two representations of the data it handles: a textual representation used to visualize the data and a logical representation that is used internally and has a richer structure than pure text. The application programmer can use and manipulate both representations. The synchronization of both representations and the mapping of high level logicBox instructions onto the lower level widget instructions of X-windows is done in a generic way. The logicBox defines a set of rules that the programmer should supply to handle all application-specific tasks.

The logicBox can be used to browse a graph. This is frequently used in the clinical workstation. Often the system has to present the user a set of options. When the user selects an option, a set of sub-options is presented. Selecting a sub-option might again list new options until the desired option is reached. This technique is used whenever the users needs to select from a list of options that is too big to show on one screen. E.g. there are over 700 Radiological examinations that can be requested. A graph structure is defined on top of this set that allows to "zoom" in on the examination wanted. Often such large sets of options need to be browsed by the users. The logicBox allows to specify only the variable parts in the form of rules. The structure of the graph (i.e. the relation between the options: the layers on top of other layers of options, and the possible paths to navigate through this structure) are specified using Prolog rules. The program code that navigates through the structure, updates screens, reacts to events, etc. is all generic code. It interprets the rules that were specified to decide on the appropriate actions.

Another high level object is a table with the possibility to create graphs based on the data in the table. The table widget is used to display all kinds of lists in a tabular format. MotifShell provides several optimized predicates to access the table, sort, read out rows and columns, etc. . . Graph-Tools is a module that given a table allows the user to create pie charts, curves, bar charts, . . . based on the data in the table. A programmer's interface to graphTools exists to make application specific charts in one command.

Optimization

MotifShell also optimizes the speed of the interface. The creation of large and complex windows can require a few seconds. In the present System applications, the user often opens an electronic form just to look at the data content and then closes it again. To avoid creating the window each time it is opened, motifShell does not destroy the window when the user closes it but hides it. When the users wants to open the window again, motifShell makes the old window visible again. The programmer can specify which parts of the window need to be re-initialized when a window is re-opened this way. This considerably speeds up the opening of windows. The performance penalty of the real creation is only incurred once for each window. If a user wants a second version of the same type of window, motifshell detects this and creates a second copy. Upon closing this second copy is also not destroyed but hidden.

The trade-off is memory: because the windows are not destroyed but hidden, the hidden representation still requires memory for storing it. MotifShell manages this memory usage and can decide to free up memory (by destroying a window) when needed. All this is completely transparent to the user: there is no difference between a newly created and a "recycled" window. The users will only incur the performance penalty related to the first-time creation of the windows, at the beginning of a newly started session with the clinical workstation. After all windows are created once (or more if the user wants more than one copy of a window simultaneously open) the system will be able to use almost only recycled windows. Most users will only open a subset of all the windows available in the clinical workstation because of locality of function. Due to locality of function, it is needed to store the hidden representation of only a subset to have all windows recycled for a specific user.

While it is often more complex to optimize on a generic level, the pay-off is greater: all applications benefit from the optimization. The overall optimization is to optimize each and every program.

MessageTools

MessageTools is the lowest module on the database side of System and the only module which directly uses the Sybase client. MessageTools has roughly three purposes: implementing generic support for the conceptual data model of the generator,
provide a higher level interface to Sybase than the Prolog—
Sybase interface by BIM, and
optimization.

Generic Support for the Conceptual Data Model of the Generator

The conceptual data model of the generator is based on a deletionless model. When the user inserts a message ("sends"), the system time-stamps it and stores the name of the user with the message. A user can delete ("omit") a message but the message is only removed from the view on top of the x#table by setting the omit flag to "o". When a user changes the data content of a message and sends this new content as a correction of the old message to the database, messageTools translates this operation into an omit of the old message, an insert of the new message and links the new message to the old one. To do this messageTools has program code that handles all messages in a generic way. It also uses specific SQL program code that was generated by formBuilder to handle those tasks that are too specific or would be inefficient to handle generically.

MessageTools works on the conceptual data model of the generator. All manipulations of the physical level of the data model are done using triggers or procedures. Most of this SQL program code is generated automatically by form-Builder.

High Level Interface to Sybase

The application programmer only calls one Prolog predicate to do an insert, omit or delete. MessageTools will query the Sybase data dictionary to retrieve the necessary information to generate SQL instructions required to perform the database operation. One call to messageTools usually results in several Sybase client calls. Because it will itself query the data dictionary it is not necessary to add a patient messageTools each time a new table is created in the system.

MessageTools is the only module that directly accesses the Sybase client software. The advantage of this approach is that all higher level modules are shielded from the idiosyncrasies of the Sybase client. Apart from making the access to Sybase simpler, this is also a maintenance advantage. Changes in the Sybase client software cause changes in one module only. Usually software changes gradually but sometimes total revolutions need to be taken care of. Sybase chose in '93 to change its client software: the current client software (DB-lib) is still maintained and supported but no new features are added to it. The new interface software (CT-lib) will gradually replace the old and it is expected that support for the old interface will be dropped somewhere in the future. MessageTools will be ported from DB-lib to CT-lib and if the changes to messageTools only can be contained, no application program will need to be adapted.

Optimization

MessageTools also optimizes Sybase access. Locality of function has as effect on the database that not all users will access all tables or views. MessageTools remembers the meta-data it retrieved locally. If a user needs the data again later in the session, messageTools retrieves it from its internal data dictionary without going to the Sybase server.

Each user needs a "process" on the database server. The client passes SQL commands to this process which executes them and sends results back to the client. Opening a process each time an SQL command needs to be processed is too much overhead, and keeping unused processes open is inefficient. MessageTools manages process use. The application programmer specifies how many processes a user can keep open simultaneously. MessageTools will allow the opening of extra processes but will close al superfluous processes after they completed their work. All this is transparent to the application.

FormTools

FormTools implements the basic System 9 metaphor: the electronic mailing of forms. It uses motifShell for the user interface and messageTools to access the database. FormTools accesses these modules via the same API (Application Programmer's Interface) as the System 9 applications do. In other words, formTools is an application to messageTools and motifShell.

FormTools makes the connection between the visual representation of the message (the electronic form) and the database table used to store the message data. It handles all standard operations on forms in a generic way, again reducing the amount of code to be written. These standard operations can be invoked from the icon bar that resides on each System form. Their functions are briefly explained:

Send FormTools checks the form procedures (see next section), sends the content of the form to messageTools which sends it further on to the database. The content of the form is stored in a table with the same name as the form. Only the content of the fields on the form with a name that is also a name of a column in that table are stored. Only the minimal data needed to reconstruct the form will be stored. These are said to be part of the message. The user does not need to specify which widgets are part of the message: FormTools accesses the Sybase data dictionary to retrieve the name of the columns and automatically builds the message from the content of the corresponding fields.

If the message is accepted by the database (database triggers perform checks on the content and may cause the insertion to abort), it is assigned a unique key (the dkey). The dkey and the name of the user who sent the form are displayed in the right hand corner of the form.

Receive FormTools will retrieve the content of all non-empty editable fields of the form. The resulting 'selection record' will be used to generate an SQL query to retrieve all records having the same values for these columns. The result is presented as a list of records.

Clear All fields of the form are cleared, that is, edit fields are emptied and check boxes are unchecked. Popup menus are reset.

Initialize The form disappears and a new copy of the original form template is drawn on the screen. If an initialization function is associated to the form, this will be used to regenerate the form.

Context Displays who sent the form and when.

Omit The form is omitted (logically deleted: it is no longer visible in the table-view but still exists on the physical level).

Correct After changing the content of the form the user can press this button to replace the old message with the new. What happens at the formTools level is highly similar to sending a form except that the dkey of the message to be corrected is passed along with the message to messageTools.

Form Procedures, Initialization and Receive Rules

If a form is defined correctly, System allows the user to add, omit and correct data without having an application program written for this. Sometimes the application needs to check the integrity of the data before allowing to store it or after storing data, the application might want to change something in another table or on the user's screen. This cannot be handled generically. To allow the application to interfere if necessary, form procedures can be defined by the application.

Form procedures are Prolog rules that will be called by formTools before and after each send, omit and correct. E.g. there are four types of that can be associated with the sending of a form: beforesend, beforeSendOnly, aftersend and afterSendOnly. Since a correction is translated into an omission and a send, the beforeSend and afterSend are also called when a message is send to correct another message. Using these rules, application specific code can be executed between the generic parts. The before-rules are typically used to do checks on data integrity that are too difficult to express in SQL. The after-rules usually perform clean-up tasks (e.g. closing a window automatically if the form was sent successfully). Many rules of the same or different types can be defined for the same form.

The initialization rules define what needs to be done when a form is opened. Usually these rules pre-fill the form with defaults (these may vary depending on the user, department, ...).

The receive rule can be used to intercept the normal way of doing a receive on a form. This is used if the generic implementation of the receive would be too inefficient. The receive rule can deduct more efficient queries based on application knowledge by looking at the parameters that are constraining the search.

Storing Only what is Needed

When discussing the sending of the form, it ghas been stated that formTools only stores the content of the fields on the form that have a name that also appears as column name in the corresponding table. Usually there are many more fields on a form than the ones that are stored. E.g. many forms display the patient's name and number, but only the number is stored. This is common practice in designing a data model. The number is used as a reference to more data (in this case demographic data) so that if any of these change, the data need to be updated in only one place (the patient identification table). All other tables refer to the patient using the unique patient number and can retrieve the correct information from this table. If the data were duplicated in every table, the correction of a simple spelling error in the patient's name would require updates in numerous tables.

Such a situation usually occurs many times on even simple electronic forms. The assignment form e.g. assigns a patient visit (e.g. an ambulatory care visit) to an assistant and a supervisor. The form (see FIG. 15) lists the name (first and last) of the patient, the number and type of the visit, and the ID, first and last name of the assistant and supervisor. Although all this information is necessary to allow the users to understand the form, only the visit number, the identification number of the assistant and the identification number of the supervisor are needed to express the relation between the patient's visit and the two physicians. The visit number is linked to the patient number via a reception table. The name of the patient can be retrieved from the patient identification table. Thus, only the three identification numbers are needed. If the form is to be understood by the users, the information linked to the numbers is to be displayed also.

Because this occurs many times on all forms, a generic solution was opted for. Just as formTools uses the table-view definition (which defines the conceptual level on top of the physical level) to insert data, it looks for the receive view to display the form. The receive view has the same name as the table-view with r# in front of it. The receive view ties the information from the different underlying tables together. FormTools uses it to display data on the form. Just as with sending, column names in the view definition correspond to fields on the form.

In a way the receive view definition acts as an application specific rule which is used by a generic application (formTools). It would be possible to specify the receive view in Prolog, but this would be much less efficient. Because it is specified as an database view, the receive view can also be used to create new views.

High Level Interface

Apart from being a generic application in its own right, formTools provides also a high level interface on top of both messageTools (Sybase) and motifShell (Motif/X-windows) to build specific applications with. Theoretically one could make any application just using formTools' functionality but this would not be ergonomically acceptable. Users want and need application-specific short cuts. This results in extra buttons and menus on the forms. FormTools provides predicates to manipulate forms that ease the implementation of such extra functions.

Users view the contents of other forms usually in the form of (work)lists. A typical user permanently switches between querying the database and adding data. The handleQuery predicate allows to specify a query and the options to display the results; it sends the query to the database, retrieves the results and displays them. Since there are many parameters that can be specified, a small interpreter was written to generate the low level program code that corresponds to each of these parameters. There is of course an overhead in creating a predicate of the complexity of handleQuery but it pays off: almost all lists in System 9 programs are generated using this predicate.

Conclusion

The goal of the present System generator is to handle as much processing as possible on a generic level. This reduces the total amount of program code and thus increases maintainability not only through code reduction but also through standardization. The richness of the tools allows faster development. The drawback is that the tools have to be built and maintained themselves. The larger the system, the larger the pay-back of such an approach since more people and more program code benefit form the same set of tools.

The present System generator is and has been constantly improved. Each repetitive programming task is scrutinized to see if it can be split in a generic and an application specific part. If so, and if it is expected to need the generic part in the future, the generic functionality is added to the appropriate module or a specific module is created. This way, the generator is constantly refined. Jean et al. advocate the use of a homogeneous platform to integrate all modules of a clinical workstation. The authors discern 4 aspects of integration: data, presentation, communication and control integration. The System generator tackles the first two of these by providing development tools. Control integration is partly modeled by the data modelling strategy (progress along the time-line of the unit of work; non-conceptual tables to explicitly store the state of this progress) but no generic software modules are provided to aid this. A generic communication module that operates on the content level of the communication stream is not yet developed. Such a module will probably be built using the Health Level Seven (HL7) communication protocol.

Development Tools

Figure 16:
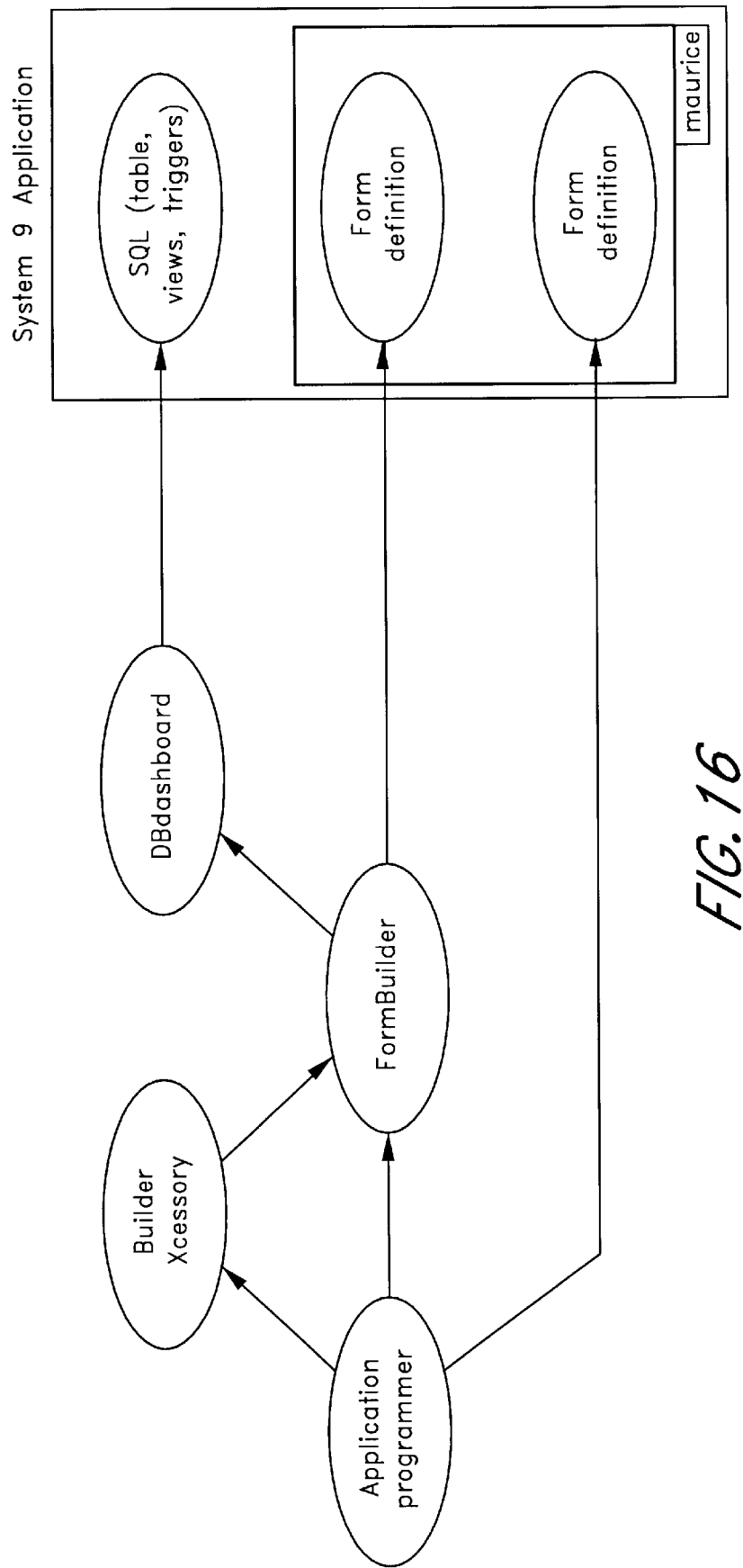
FIG. 16 is an illustration of a system application development using builders.
Figure 17:
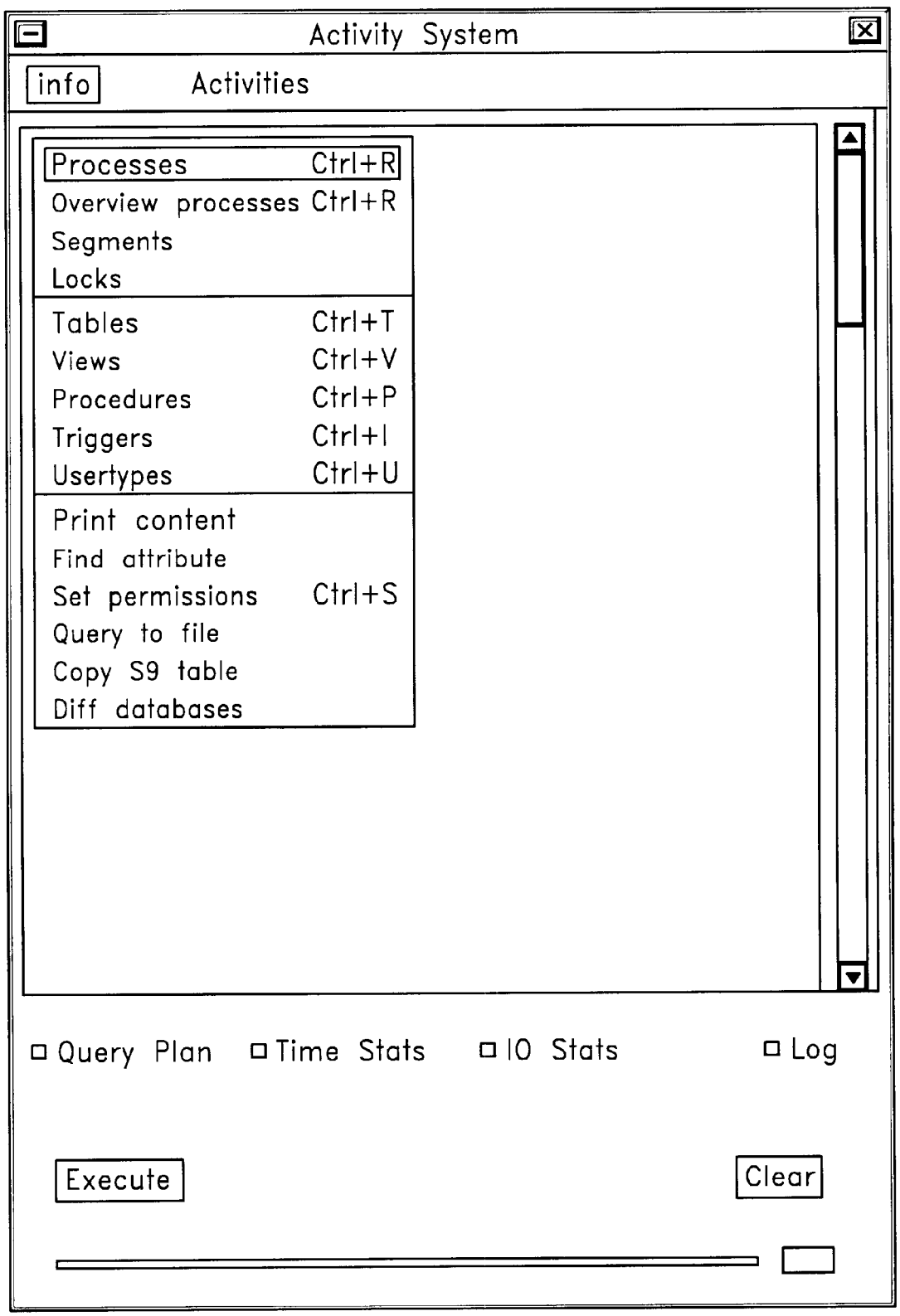
FIG. 17 is an illustration of a DbDashboard main menu.
Figure 19:
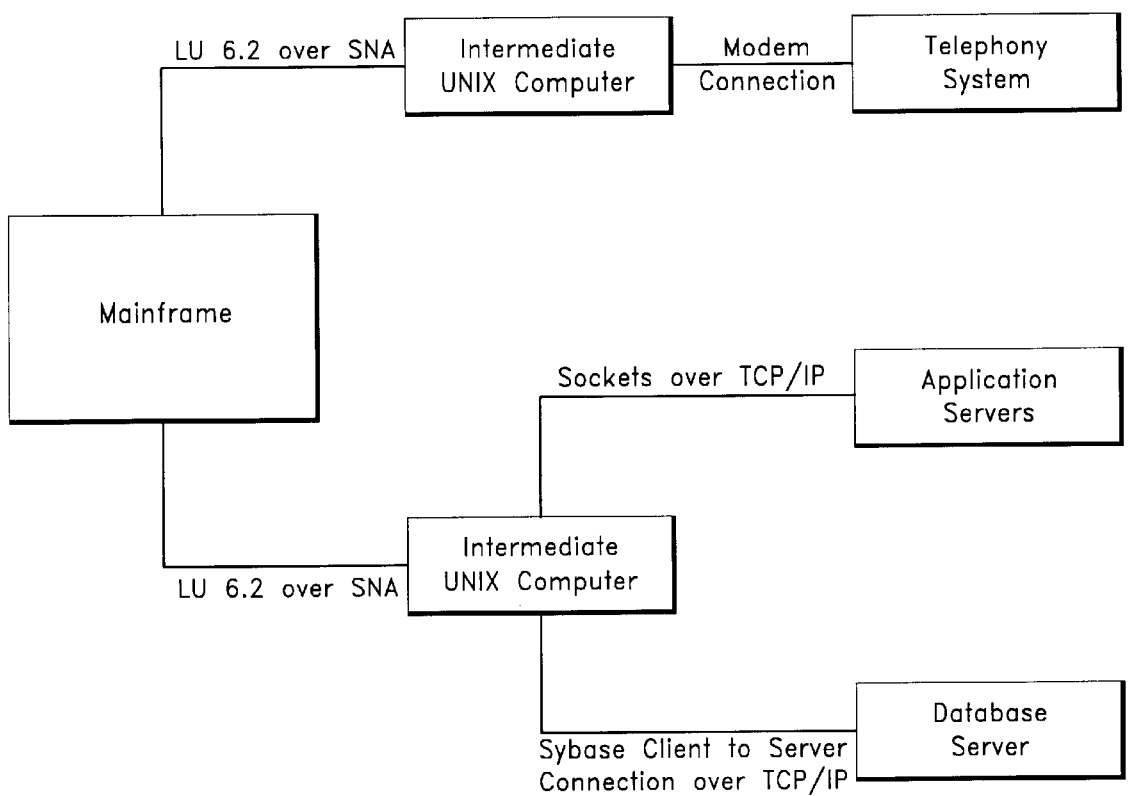
FIG. 19 is an illustration of LU 6.2 connections.
Figure 21:
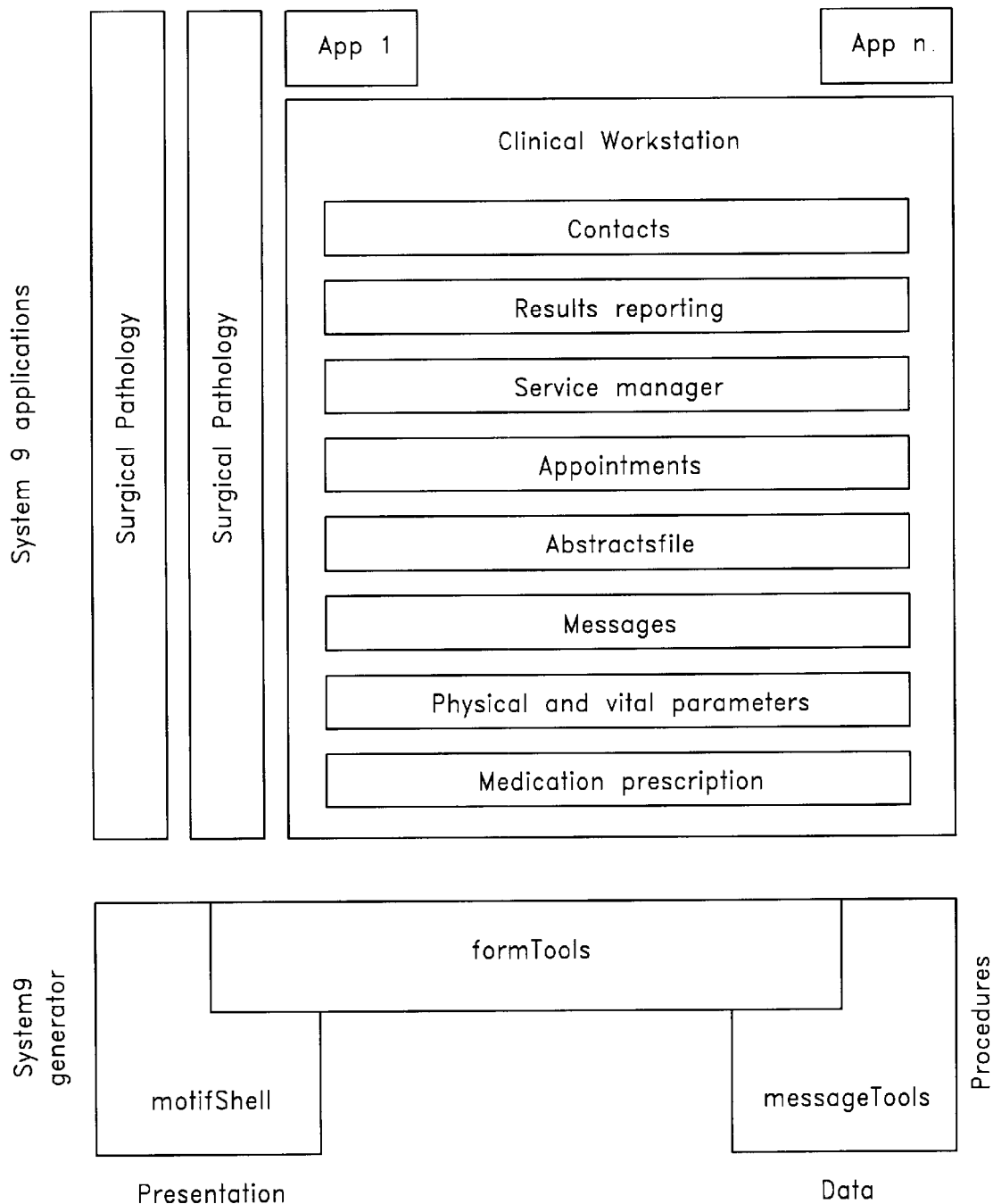
FIG. 21 is an illustration of a software architecture of system applications.
Figure 22:
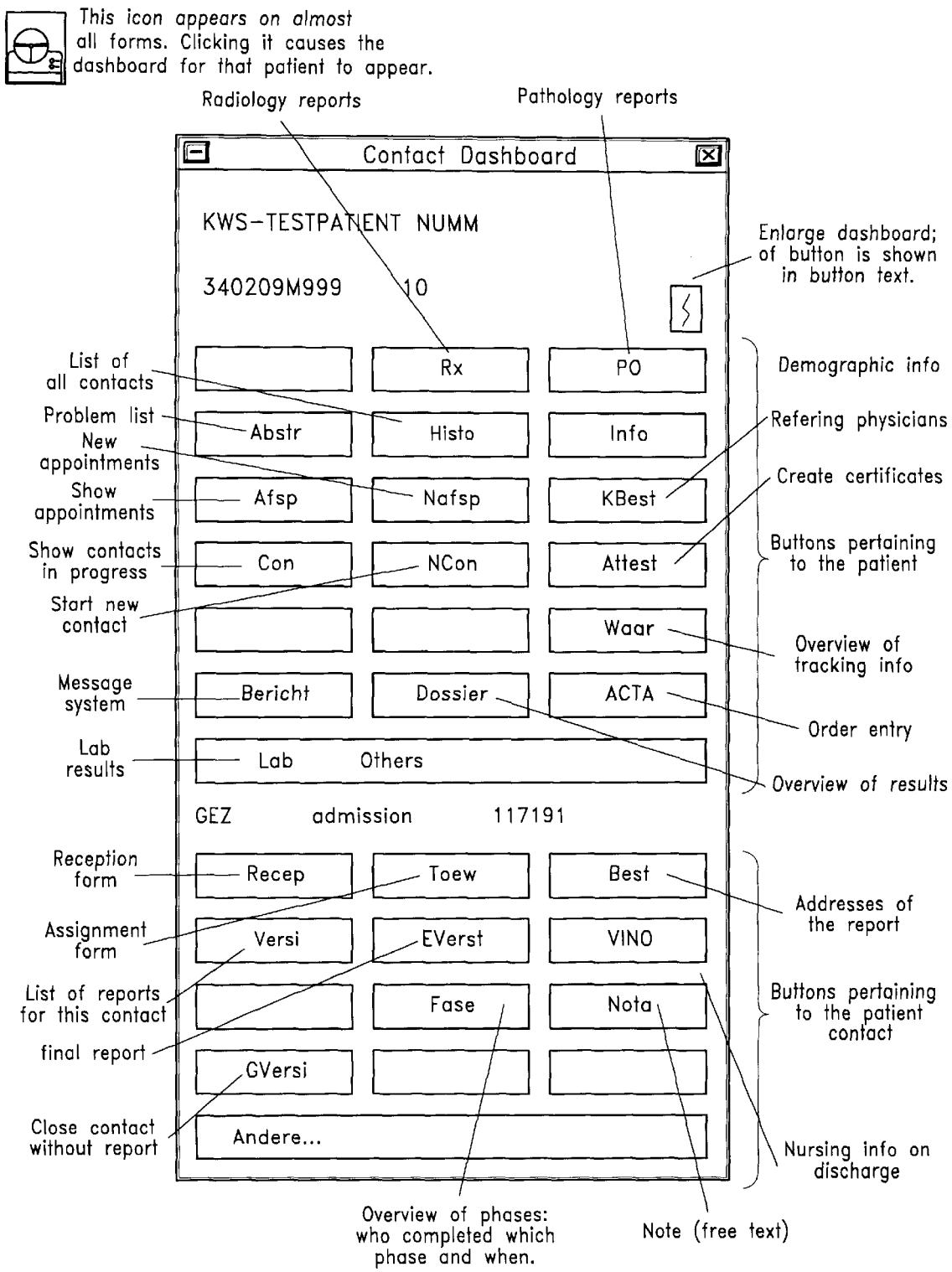
FIG. 22 is an illustration of an explanation of the buttons on the dashboard.
Figures 23, 24:
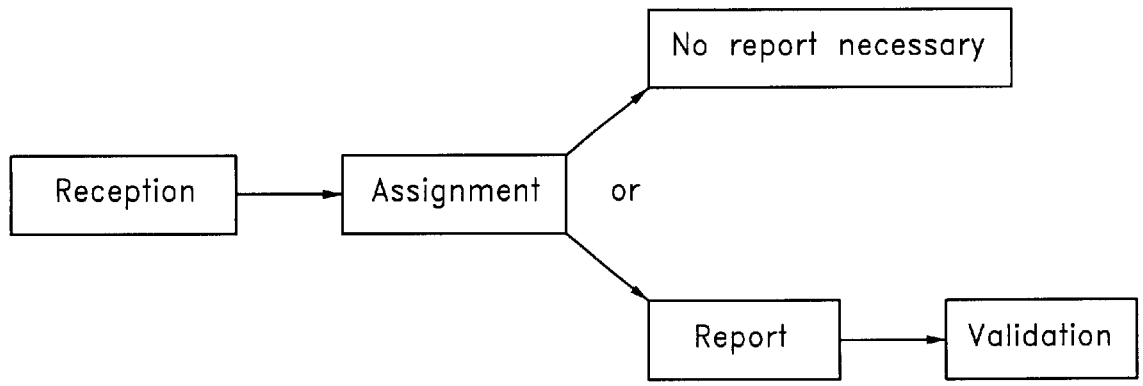
FIG. 23 is an illustration of mandatory phases of a contact.
FIG. 24 is an illustration of a conceptual data structure of a slot manager.

To automate and speed up the development process, several development tools have been developed. One (BX) was bought. Their use in the development process is shown in FIG. 16.

Builder Xcessory

Builder Xcessory or BX is a graphical user interface design tool from ICS. With BX the programmer can "paint" a window. The programmer begins by drawing the rectangle of the top level window. All available widgets or display items can be chosen from a palette and put within this window. The relations between the display items (e.g. the alignment, size, shape, . . . ) can also be set here. After specifying the visual aspect of the window. BX can generate the creation function for this window in the programming language C.

The application programmer does not change this creation function. It is linked to a Prolog predicate so that it can be called from the System applications.

FormBuilder

FormBuilder was developed to automate the generation of the database objects associated with electronic forms. After painting the form using BX and generating the creation function, the programmer uses formBuilder to generate SQL. FormBuilder creates the form using the creation function. The user then specifies the fields to be stored in the database by clicking on them. Then the types (integer, character, real, . . . ) can be specified. Eventually the SQL to create the table, the table-view and the generic parts of the triggers to support the integrity of the physical level of the data model, are generated. FormBuilder generates the SQL code and presents it in SQL windows of dbDashboard where the programmer can add the application specific parts. FormBuilder is a rule based system that contains rules for each of the SQL parts to be generated.

DbDashboard

Because only the standard part of the SQL can be generated and stored procedures and triggers need to be maintained, a tool was developed, that facilitates creating and editing database objects and that is integrated in the System environment. DbDashboard provides a window from which SQL can directly be sent to the database. Options to generate time and input/output statistics and to have the optimizer print out the query plan can be set from this window. DbDashboard provides (amongst others) menu options to create and maintain tables, views and procedures, add comments to them. It creates SQL code to set permissions and can be used to check differences between databases (e.g. test and production databases can be compared).

DbDashboard is available to developers only. It is intended to add tools to migrate tables, views and procedures from the test to the production database.

Maurice

To automate part of the debugging process a program checker called Maurice has been developed. It is a Prolog program that can read another Prolog program and try to detect bugs. It consists of three parts: the inference engine, the standard Maurice rules and the specific Maurice rules. The inference engine reads the code and applies the standard Maurice rules to it. Standard Maurice rules may invoke specific Maurice rules.

Standard Maurice rules check for suspicious code. E.g. typing errors in variable names are a common cause of bugs. Maurice will check for variables that appear only once in a predicate and report them. Usually a variable will appear more than once in a predicate: the first time to instantiate it (give it a value) and further on to do something with that value. A variable that just "sits" there is suspicious and is reported, e.g. if Maurice reports that it found two "lone variables" called _myVariable and _myVarable the programmer will immediately know that he made a typing error. Program code that calls a predicate that does not exist is also suspicious: probably it is a (typing) error since it makes no sense to try to use something that does not exist.

Maurice also: logs into the database as a user. If it detects that the program will try to use a database object (most often a procedure) it will check if this procedure exists in the database. For each of the System modules of the generator a corresponding Maurice rule base exists to check for the correct usage of the programmer's interface it defines. E.g. if the program tries to set the value of the field A on the form B, Maurice will check if the form definition for form B exists and if it contains a field definition for field A.

Tools

The following modules are sets of tools that are very general in nature. They were developed to be used in several System applications.

S9Services

This module was developed to hold medical building blocks that are needed in most applications but that are not general enough to be implemented in the generator. Examples of such building blocks are: tools to store patient information within an application, graphMaker (i.e. a tool to create and browse a graph of options), explicit access control checks, smartAsk (functions to automatically and intelligently generate windows to request data from the user), . . .

Text Assistance

Many acts in the hospital end with one physician writing a report to another. Some of these can be standardized. These reports can be generated by asking the clinician to specify the relevant parameters and then generate text based on the value of these parameters. This has two advantages: by having the computer ask for the parameters, the reports become more standardized and no parameters can be forgotten (there is no difference between paper or computerized structured reports. The second advantage is that it takes much less time to generate such a report.

To facilitate the programming of text generating procedures, a specific language has been developed. The language looks more like a conventional programming language and has a syntax totally different from Prolog. These text generating programs were compiled into Prolog data structures. Text assistance provides an interpreter that generates a report, given a set of parameters, their values and a compiled text assistance program.

UZ PrologTools

UZPrologTools is a module which was developed to function on the lowest level (i.e. it does not use any other module) but is itself used by almost any module in the system. It contains a set of small but handy predicates to facilitate programming. E.g. a set of predicates to read and write records of fixed length, a debugging tool, list manipulation predicates, . . .

Connection Between the Mainframe and the System Environment

A fast bi-directional link is necessary between the administrative system on the mainframe and the System environment.

Link Between the Mainframe and the System Databases

To insert and request data from a Sybase database, the choice was made for an interface that would allow a (COBOL) program to execute an arbitrary stored procedure in Sybase. The COBOL program that wants to communicate with the Sybase server, first sets up an LU 6.2 connection with an intermediary UNIX machine. LU 6.2 is a standard for peer-to-peer program communication. This is a direct communication between two programs running on (possibly different) computers. It sends a data string over this connection to a transfer program on the intermediary machine. This transfer program is equipped with the Sybase client software. It sends the string to the Sybase server which executes it. If the data string is a query, the transfer program retrieves the results and transfers them back to the requesting program on the mainframe.

LUTools

LUTools allows to set up a LU 6.2 connection from within a System application with the mainframe. LUTools provides a high level Prolog interface on top of the LU 6.2 libraries provided by the computer manufacturer. With LUTools an arbitrary CICS18 transaction can be executed. The transaction can return data to the Prolog program. It is used to communicate with the mainframe system to retrieve e.g. laboratory test results or to insert data into the billing system.

Order Entry in System: the Service Manager

The service manager uses a generic framework to handle services. It defines the generic storage structure of services, the operations that can be done on services (request, perform, annul and close) and the framework for the user interface. The framework is completed by user defined rules that allow to define the specific parts. An overview of the service manager framework will be now given.

Storage Structure for Services

Problem

The data for such services is structured but since there are so many different acts that may be requested, the number of structures necessary to implement them all is huge. For this reason it is infeasible to store each type of structure in a separate file or database table. Most of these tables or files would be small and reintegrating data on screen from all these objects to give a global overview of a patient is too inefficient to achieve an acceptable response time.

The solution could be either to limit structure to some greatest common denominator or to make a very general structure that subsumes the specific ones. The second option was chosen. To do this some constraints of using a relational databases had to be solved. A relational database is very strict in the storage structures it allows: the only structure allowed is the table. The columns of the table are fixed in number and type and need to be predefined. Altering the structure of a table usually means stopping the programs that use it, change the table definition, install programs adapted to the new structure and restart them. This is cumbersome and cannot be done each time a new act needs to be defined.

Solution: Translate Generalized Table Structure to Specific Logic Terms

To store the acts generalized tables were used. These tables can accommodate the storage of any service. There are four basic tables that the service manager employs: request, perform, annul and close. A service can be directly performed without it being requested or it can be requested and then performed or annulled (both close the request). Some requests are continuous requests, these are requests that stay open even if the service is performed (e.g. for requests that have to be performed several times). Continuous requests have to be closed explicitly. (For simplification, only the request and perform tables will be used to discuss the underlying principles of the service manager).

Services are grouped in types. A service type collects all services that logically belong together. E.g. there is a separate service type for the radiology request/perform system and another for general medical activities. For each of these types a separate set of these four base tables exist.

The service manager tables constitute of three parts: the standard, fixed and variable part. The standard part defines the columns that are the same for all service types but differ between request and perform. The fixed part defines the columns that are fixed for a certain service type. The variable part is where the flexibility of the service manager lies. The variable part is a set of columns of different data types and different lengths. The columns that can hold an integer number are called int1, int2, . . . ; the columns that can be used to store a bit value bit1, bit2, . . . etc.

While the columns of the standard and fixed parts have one interpretation for all rows in the table, the columns of the variable part have an interpretation depending on the service stored in the row. Each service can have some attributes that need to be stored (e.g. a number, the name of a medication, type and number of materials used, . . . ). These parameters are mapped on the physical columns of the variable part. So the column called int1 can hold the number of incisions that were used for a certain type of surgery but in another service it can hold the number of catheters used. The logical structure of a service is thus mapped onto the generic table structure.

The service manager operates on the generic level of the four base tables. It uses user defined rules to access the specific tables used to store the service requests and performs of a given type. Several types can use the same set of tables but one type must be stored in one set of tables. The translation between the storage structure and the logical structure of the service is also done by rules. As soon as a service is retrieved from the database it is translated to its logical structure. Before storing a service request or perform in the database the logical structure is again translated to the structure of the table. Translation rules can be defined for a whole type or for a specific service.

Auxiliary Tool: Service Type Maker

The structures needed to define the mapping between the logical and the physical representations are quite large and thus error-prone. To aid in the construction of these structures a program was written that allows to define parameters for a service and specify the physical storage type. The service type maker then deducts the optimal mapping structure for this service and generates the Prolog code for it.

User Interface

A generic user interface was also constructed. The basic structure of the interface consists of a selector, an editor and a collector. Consider requesting a service (to perform services is highly similar). The selector is used to select a service request. When a service request is selected its parameters can be edited in the editor. A default editor is supplied, but for those services that have extra parameters, the service manager will either construct a window to request values for these parameters or the application can define a special editor that will be used by the service manager. After editing, the service request can be sent to the database. The collector then shows all services requested for a patient. Since there are many different types of services (each with their own set of parameters) that all need to be shown in one collector, only a textual representation of the services can be displayed. A rule base is used to transform the logic term representation of the service to a textual representation which is shown in the collector.

The service manager combines functionality of many other modules already discussed earlier:

service requests and performs can be sent, corrected or omitted. They are implemented as System messages;

the service manager calls equivalents of the form procedures before and after each database operation. Using access predicates defined by the service manager the user can access the logic representation of the service objects;

the selector and collector use the logicBox. The selector often uses the logicBox to navigate through a graph (see FIG. 14).

The selector interacts with the editor and the collector via the standard selector protocol. This allows to create specific selectors if need be. The selector is subject to much ergonomic constraints. The ideal selector is one that guesses the next service to be requested. To allow fast selection of the most common services specific graphs for each department or ward are created. E.g. the Radiology request graph starts with the top 20 most requested Radiological examinations for each department.

Apart from browsing the graph of services, the user can also type in part of the description of the service and then search the database for matching services. Once the users are familiar with working with the keyboard this is often the fastest method of retrieving an option from a very long list. Teich et al. take this even a step further. Next to selecting from a hierarchical options list, they implemented a sort of command line interface where partial orders can be typed in. Upon pressing "enter" the system searches for matches and tries to expand the order(s). This allows not only to type in more orders in one batch but also to type in the parameters directly as well.

To speed up selection of the most common activities the grid was added. The grid is a rectangular matrix with 54 cells containing abbreviations of the 54 most common services for a particular ward. When opening a service manager window, the system tries to guess the probable location of the patient. This ward number is used to find the appropriate rule to fill the grid. The cells in the grid act as buttons: clicking a cell moves that service to the editor. The grid gives additional one-mouse-click-access to 56 services. Because the grid adheres to the standard selector protocol, the editor and collector did not need to be adapted when the grid was added.

One of the main problems in creating a user interface is the difference between first-time or occasional users and experienced or power users. The first category requires a verbose interface and navigating through a graph or a hierarchical set of options allows them to contemplate every step. The novice or occasional user is confused by too many shortcuts and cannot memorize them since he does not use the system often enough.

The experienced user knows exactly what he wants and where it is located in the system and will always require a larger set of shortcuts that brings him with as few mouse-clicks as possible to the location he wants. In the grid all options are in a fixed location. Experienced users can select an option motorically without reading the contents of the cells.

The Clinical Workstation
Introduction
Active Participation of Clinicians in the Specification: the Sounding Board Group The Surgical Pathology and Radiology systems were developed by discussing the specifications with key clinical users of the departments. Not only functional specifications were discussed but also the underlying data model. The use of the message modelling concepts facilitated this approach.

The hospital management selected four clinical specialists from different disciplines and one nurse to serve as a sounding board to the developers. All members were of senior rank and had extensive experience in a clinical setting. After 9 months the head of the administrative department and the head of the pharmacy joined the group.

The group met with the development team for almost a year every week during a 2 hour meeting. All design decisions were presented to this group. Later in the development prototypes were used to advance the discussion.

One Medical File, One Set of Procedures

Central to the design of the clinical workstation is the idea of an integrated medical file. Not only would the data be contained in one database, the functionality would be identical on all wards. Being a teaching hospital, many of the physicians have change departments frequently. If the functionality would differ too much this would present a training problem.

One of the main tasks of the sounding board group was to warrant that the functionality was kept sufficiently general to implement on all wards. They spotted where customization would be required. Automating an organization changes the workflow and thus procedures must be adapted. The sounding board group also defined the procedures that all departments must use when working with the clinical workstation.

Software Modules of the Clinical Workstation

The clinical workstation currently consists of 8 modules. All but two (registration of vital and physical parameters and medication prescription) are in production.

To the user all these modules are integrated via the dashboard.

The dashboard in the clinical workstation consists of two parts: a patient linked part and a contact linked part. Figure—shows the dashboard and explains the function of the buttons. The dashboard is a navigation instrument: the buttons activate a module of the clinical workstation. Most forms have a dashboard icon on them. Clicking this icon retrieves the relevant dashboard. The dashboard takes the user to the forms and vice versa.

The Contact Module

The contact module is the main module of the clinical workstation. A contact can be an outpatient visit, a hospitalization, a gastroscopy, an operation, a stay in intensive care, a chemotherapy treatment, . . . All patient contacts are monitored using this module. A contact differs from patient admissions (or transfers) in the sense that one contact can have many admissions (e.g. a renal dialysis treatment will have an admission each time the patient is dialyzed) On the other hand, one admission can have several (simultaneous) contacts. E.g. a surgical patient will have an open contact for the surgery department and may have a separate one for the operation itself. A stay in the ICU might also cause another contact to be opened by the physicians of the ICU. A contact is a medically logical unit, as opposed to a patient movement (admission, discharge or transfer) which is a movement in time and space. When the patient is discharged the contact will usually not be closed. The contact is closed when the unit of work is completed.

A contact has several phases, some of which are optional. The phases of the contact make up a unit of work. Each of the phases are represented by an electronic form (for an example of the assignment form. The contact starts with a reception form. This links the contact to a patient, and a department (e.g. pediatric Nefrology). The type (inpatient, outpatient, . . . ) is also determined here. The second phase, assignment, assigns the contact to a physician and a supervising physician or supervisor. The unit of work needs to be completed either by the validation of an medical report or by the explicit statement that no report was necessary for this contact.

The data captured by the contact module governs most of the workflow for the physicians. Especially the first two phases capture the information necessary to steer the workflow. The reception form gives the data to divide the work among the physicians of a (sub)department using the assignment form. These data are subsequently used to make worklists for individual physicians (such as a list of reports that need to be written or, for a supervisor, the list of reports that are ready to be validated).

The most important piece of data captured in the contact module is the medical report. One of the main products of a hospital is information (to the patient, the treating physician, . . . ) and most of this information is under the form of a medical report from one physician to another. In a teaching hospital, many reports are written or dictated by physicians in training. These reports need to be validated by a supervisor. An unvalidated report can be printed but "unvalidated" will be printed obliquely over it so that it is easy recognizable. After validation the reports can be printed. Subsequently they are signed and mailed to the (external) physician who referred the patient.

Optional Phases or Forms

Several other forms are linked to a contact but are optional. The note allows to attach a small note to the contact (akin to post-it notes). Intermediary reports allow to report progress without closing the contact. This is used for long term contacts: a renal dialysis or chemotherapy episode is usually represented as one contact. The VINO (Verpleegkundige Informatie Nota bij Ontslag—Nursing Information Note at Dismissal) is used to give information to the patient concerning medication, personal care, . . .

Organizational Problem Caused by Automation

Before the automation, reports were typed out centrally by typing clerks or by secretaries of the department. The letter to be signed stayed with the paper file, was signed and returned with the paper file for further handling. The report and the paper file usually travelled together.

With the clinical workstation, validation is done on screen, and can be done on any terminal in the hospital. This causes work to be shifted from the secretaries to the supervisors. A supervisor can validate a report without the paper file since most of the data are available on-line; he does not need to wait for the paper copy. As soon as a report is written, it appears on the validation list of the supervisor. When the report is validated, it is automatically printed in several copies (one for the referring physician, one for the medical file, a personal copy, . . . ). The problem is that the supervisor ends up handling the physical copies of the report and is responsible that they reach their destination.

This was solved by using "electronic signing". The problems arise where the flow of the report changes from electronic to paper. This has to be at the validation phase when a written signature is needed. An addition was made to the contact module to dissociate validation from printing and signing. When the report is validated, it moves to a print list. The secretaries are responsible for handling the print list. Either the reports are signed in batch at the secretary's office or better still, the physical signature is replaced by a notice at the end of the report stating "this report was electronically signed by dr. xyz at date dd.mm.yy".

Migration Problem: Historical Data

Another encountered problem was one of migration. Most of the departments already used computers to type the medical reports. Different departments had different computer systems. A possibility to overcome this major problem, could be the creation of a historical database, load all data and link the historical database to the clinical workstation. Different source systems would result in different historical databases and the user would see a difference between data from the historical system and data from the new system.

Instead a load program was developed to read in the historical data and to translate the historic data model to the data model used in the corresponding application. The load program uses a rule base to make an educated guess for the missing data. If information cannot be deduced or guessed at all, sensible but recognizable defaults are entered. This technique was applied for the first time in Radiology. 244.451 radiological reports could be retrieved this way. It was repeated for Pediatrics (94.866 reports), Oncology (26.727 reports), Gynecology/Obstetrics (96.518 reports) and Hematology (45.266 reports).

The main advantage is that it populates the system with data as if the department has been working with it all along. There is no difference in structure between historical data and new data, but certain data items might be missing or set to defaults. No extra software needs to be written to create and integrate the historical database with the System applications.

The disadvantage is that disk space is wasted on storing millions of default values that were generated by a computer and thus carry no informational value. At current disk prices this cost is easily offset by the cost of developing specific software for a historical database. The other disadvantage is that the load program is more complex since it must translate one data model into another and generate or deduce data were needed. This has to be repeated for every type of load but this is a one-time effort and some of the software can be reused by using again the technique of inference engine and rule base.

Appointment System: Slot Manager

The appointment system is called the "slot manager". The appointment books for scheduling outpatient visits consist of many empty slots. The number of slots per resource and per day is limited and predetermined. The slot manager manages the electronic equivalent of these paper books. It uses a gigantic grid of slots: the X-axis is the (start) time and the Y-axis the resource (a physician, but it can also be an operating theater, a procedure, . . . ). Each slot also has a duration associated with it. If a patient number is stored at the intersection of time T and resource A, this means that resource is allocated to that patient for the duration associated with the slot.

The advantages of the slot concept are that very little checking needs to be done at the time of booking: if the slot exists and it is empty it can be booked. It is not necessary to check for double bookings or if the resource will be available at all. All this is verified once when the electronic appointment books are created. Searching for the free slots for a resource (e.g. when a patient wants to see a particular physician) is done by accessing the matrix of slots via the Y-axis. The disadvantage of this approach is that all slots need to be predefined long beforehand (at least a year; for oncology two years), and this takes up space. It also requires the physicians to decide long beforehand when and how long they allow appointments to be booked.

An alternative approach to build an appointment system is to have one large free space of time and resources and check, at the time of booking, if the resource is available. Instead of explicitly stating which slots are available, there are rules that define what is allowed and what is not. Slots not yet occupied do not take up space but the booking becomes much more time consuming because these rules need to be checked for each booking. E.g. if patient A wants to see physician B Tuesday at 10:00 h, the system needs to check if B is available for outpatients at that point in time, and is not yet booked for another patient in an overlapping time frame. The system also needs to check if the maximum number of patients for that day for Dr. B is not yet reached (to avoid overbooking). Searching for any physician from the department of pediatrics that is available for an outpatient visit is much more time consuming.

Because the booking process (finding a free slot and placing a patient in it) needs to be fast (usually somebody is waiting for an answer) the first design was used. Free slots are searched using a query screen where several search criteria can be entered. The free slots qualifying the search criteria are listed and selecting one of these puts the patient in the slot. The system discerns between book owners and other users. Normally users can only see free slots and never get a list of all patients booked for a particular day or physician for reasons of privacy. They also cannot overbook. A book owner both can overbook (i.e. create duplicate slots) and see the list of patients that are booked in the electronic books he owns. Book owners can tie information to slots (e.g. "no new patients; only for follow-up"). The booker of the slot can add information about the patient to the slot.

The advantages of electronic appointment books are:
patients are always identified correctly and readably;
the appointment data are transferred electronically to the medical archive to retrieve the paper files. They are also loaded in the administrative system so that when the patient is admitted the correct data can be pre-entered and the admitting process is sped up;
appointment books are accessible from any point in the hospital instead of only at the appointment desk;
it is possible to give an overview of all appointments for a patient.

Auxiliary Tool: Slot Maker

Because slots constantly need to be added a slot maker program was written. This program takes a pattern of slots for a book (e.g. every Monday, Friday at 9:00, 9:15, 9:30, 10:00, 10:30, . . . ) and generates the rows in the table that represent the slots. This is again a rule driven program.

Conflict with Deletionless-ness of System Data Model

The slot manager needs all slots to be ready-made before they can be booked. The users update them. This is not an additive data model and implementing it as one would be senseless: the first sender of the slots would always be a program (the slotmaker) and all real operations would be corrections. Because the log of all operations on the appointment books (which is an implicit advantage of using a deletionless data model) is not wanted to be lost, all changes to the appointments are logged in a separate table using Sybase triggers.

Service Manager

A lot of the communication in a hospital between care providers is requesting and reporting some sort of act that is (to be) performed on a patient. Order entry for Radiology or laboratory tests, requesting nursing act, gastroscopy, ECG requests, . . . are all examples. This is often called act management and some projects intend to define a generic framework for it.

Order entry is a part of act or service management. As early as 1970, Maurice Collen advocated that "physicians should enter their medical order directly into the computer" for reasons of accuracy and completeness. Many order entry systems fail(ed) but in the early 90's there was a renewed emphasis on physician order entry owing to several important factors:
the advances in computer technology thus allowing better user interfaces;
an increase in computer literacy with health care providers of all levels; and
the interest to develop a complete computer-based patient record to increase the quality of care.

Advantages of Physician Order Entry are Manifold all orders are legible and complete (the software can block a request until all mandatory fields are completed but this is no guarantee that the data entered make sense);
orders reach the service department immediately;
orders cannot be lost and pending orders can be reviewed.

TABLE 1

Tables partaking in the example query

| Table | Function |
|---|---|
| patienten | Demographic data for all known patients. |
| x#receptie | Attributes a contact number to each unit of work and links it to a patient; all subsequent phases pertaining to that contact share the same number. |
| x#artsSup | Relation between contact number and ID of assistant and supervisor |
| x#verslag | Contains all reports. A contact can have several intermediate reports but only one final report (designated by the report type "eindverslag"). Each report has a report number. This table links report numbers to contacts. |
| x#validatie | Contains the report number, contact number and the ID of the supervisor who validated the report. |
| x#S9User | Contains descriptive information (name, department, telephone, . . .) on all users of the system. |

TABLE 2

Order of table accesses in query 1

| | |
|---|---|
| x#verslag | Table Scan (to create worktable) |
| x#verslag | Table Scan (group by) |
| x#validatie | Index: verslagNr (to create worktable) |
| Worktable | Table Scan |
| x#verslag | Index: verslagNr |
| x#artsSup | Using Clustered Index |
| x#receptie | Using Clustered Index |
| allePatienten | Using Clustered Index |
| x#S9User | Using Clustered Index |

TABLE 3

1 Query plan for query 1

STEP 1
The type of query is SELECT (into a worktable).
GROUP BY
FROM TABLE
x#verslag
Nested iteration
Table Scan
TO TABLE
Worktable
STEP 2
The type of query is SELECT (into a worktable).
GROUP BY
Vector Aggregate
FROM TABLE
x#verslag
Nested iteration
Table Scan
FROM TABLE
x#validatie
Nested iteration
Index: verslagNr
TO TABLE
Worktable

TABLE 3-continued

STEP 3  
The type of query is SELECT.  
FROM TABLE  
Worktable  
Nested iteration  
Table Scan  
FROM TABLE  
x#verslag  
Nested iteration  
Index: verslagNr  
FROM TABLE  
x#artsSup  
Nested iteration  
Using Clustered Index  
FROM TABLE  
x#receptie  
Nested iteration  
Using Clustered Index  
FROM TABLE  
allePatienten  
Nested iteration  
Using Clustered Index  
FROM TABLE  
x#S9User  
Nested iteration  
Using Clustered Index  
11.2 Query plan for query 2

STEP 1  
The type of query is SELECT.  
FROM TABLE  
statusContact  
Nested iteration  
Index: usernameSup  
FROM TABLE  
x#S9User  
Nested iteration  
Using Clustered Index  
FROM TABLE  
x#verslag  
Nested iteration  
Using Clustered Index  
11.3 Query plan for query 3

STEP 1  
The type or query is TABCREATE.  
STEP 2  
The type or query is INSERT.  
The update mode is direct.  
Worktable created for SELECT_INTO.  
FROM TABLE  
x#artsSup  
Nested iteration  
Index: usernameSup  
TO TABLE  
Worktable  
STEP 1  
The type of query is DELETE.  
The update mode is deferred.  
FROM TABLE  
supervised  
Nested iteration  
Table Scan  
FROM TABLE  
x#verslag  
Nested iteration  
Using Clustered Index  
FROM TABLE  
x#validatie  
Nested iteration  
Index: verslagNr  
TO TABLE  
supervised

TABLE 3-continued

STEP 1  
The type of query is SELECT.  
FROM TABLE  
supervised  
Nested iteration  
Table Scan  
FROM TABLE  
x#S9User  
Nested iteration  
Using Clustered Index  
FROM TABLE  
x#verslag  
Nested iteration  
Using Clustered Index  
FROM TABLE  
x#receptie  
Nested iteration  
Using Clustered Index  
FROM TABLE  
allePatienten  
Nested iteration  
Using Clustered Index

TABLE 4

Performance results. For the three queries the number of table scans, CPU time and elapsed time are compared.

| | | Number of table scans | | |
|---|---|---|---|---|
| | Size (#rows) | Query 1 | Query 2 | Query 3 |
| x#receptie | 132.043 | 6 | | 6 |
| x#artsSup | 132.374 | 454 | 6 | 1 |
| x#verslag | 158.371 | 456 | | 2.248 |
| x#validatie | 114.391 | 114.040 | | 1.053 |
| x#S9User | 1.789 | 6 | 6 | 600 |
| allePatienten | 1.055.629 | 6 | | 6 |
| statusContract | 7.772 | | 1 | |
| #validated | | | | 2 |

| | Timing | | |
|---|---|---|---|
| Server CPU time (msec) | 129.000 | <100 | 1.700 |
| Elapsed time (msec) | 129.746 | 446 | 3.055 |
| Ratio elapsed time | 291 | 1 | 7 |

TABLE 5

Disk overhead of the non-conceptual tables. The total of the non-conceptual tables and of each database is shown. The overhead of the non-conceptual tables expressed as a percentage of total database size decreases with time.

| | Surgical pathology | Radiology | Clinical workstation |
|---|---|---|---|
| Months operational (Aug. 95) | 59 | 38 | 8 |
| Non-conceptual tables (Mb) | 1.2 | 4.49 | 15.08 |
| Total DB size (Mb) | 1641 | 4121 | 844 |
| Overhead (%) | 0.07% | 0.11% | 1.79% |

TABLE 6

Summary of effect of scaling up the number of users, size of the application or amount of data of a System 9 application on the presentation workstation, application server or database server.

| Hardware Application | Presentation workstation | Application server | Database server |
|---|---|---|---|
| Number of users | Trivial: one per user | N users per application server depending on the processing power and available memory | More processing power and memory needed |
| Size of the application | No influence | Increase the amount of virtual memory per user | No influence |
| Amount of data | No influence | No influence: only transient data and kept here | More disks needed |

What is claimed is:

1. A relational database compiled/stored on a computer environment for storing and querying data about units of work, said relational database comprising:
   a first set of tables comprising first columns and first tuples and a first dataset containing first data comprised in said first columns and first tuples; and
   a second set of tables comprising second columns and second tuples and a second dataset consisting of second data, all the data comprised in said second columns and second tuples being second data, said units of work comprising first services, final services and current services, said unit of work having a status being inactive, active or terminated, wherein said second data is a redundant representation of a part of said first data.

2. The relational database of claim 1, wherein the second data is identical to the first data comprised in at least one first tuple.

3. The relational database of claim 1, wherein the second data is derived from the first data by an adaptation of a part of the first data comprised in at least one first tuple.

4. The relational database of claim 1, wherein the second data is derived from the first data by an operation on a part of the first data comprised in at least one first tuple.

5. The relational database of claim 1, wherein said first data comprises all said services of all units of work having an active or terminated status, and said part of said first data consists of all the current services of all units of work having an active status.

6. The relational database of claim 1, wherein said second data support a query within said first data whereby the performance of said query within said first data is increased.

7. The relational database of claim 6, wherein application programs executing the query are compiled/stored on said computer environment and said relational database is adapted for access by said application programs.

8. The relational database of claim 7, further comprising programs being executed while data is added to a selected table of said first set of tables whereby said program generates said second data of said second set of tables.

9. The relational database of claim 1, wherein said first set of tables comprises a physical level, a conceptual level or an application level.

10. The relational database of claim 9, wherein each of said data is an electronic message capable of representing contents of electronic forms.

11. The relational database of claim 10, wherein said electronic messages represent essences consisting of a group of processes, operations, services, acts, objects and persons within a defined world.

12. The relational database of claim 11, wherein said defined world is a hospital.

13. The relational database of claim 10, wherein a set of messages is related as a unit of work.

14. The relational database of claim 13, wherein said unit is represented by at least one tuple in said second set of tables, said tuple representing said unit within said second set of tables being deletable.

15. The relational database of claim 1, wherein one of said first and second data is in one tuple, each of said first data being permanently stored in one tuple being added to a table of said first set of tables, whereby the first set of tables is deletionless and additive.

16. The relational database of claim 15, wherein said tuples containing said first data are labeled according to the operation creating said first data, said operations selected from a group including inserting, omitting and correcting said first data.

17. The relational database of claim 16, wherein said tuples containing said first data are labeled according to a creator creating said first data, and according to the date of the operation creating said first data and according to the link between a new version of said first data and an old version of said first data.

18. A method of constructing a relational database for speeding up the execution of a predefined query within said relational database, said relational database comprising data concerning units of work, said units of work comprising subsequent services, said services comprising a first service, a final service and a current service, said unit of work further having a status, said status being inactive, active or terminated, and said predefined query being a query at least partly within an unit of work having an active status, said method comprising:
   creating simultaneously a first and a second set of tables, said first set of tables comprising first columns and first tuples and a first dataset comprising first data located in said first columns and first tuples, and said second set of tables comprising second columns and second tuples and a second dataset consisting of second data located in said second columns and second tuples, said second data being a redundant representation of a selected part of said first data; and
   storing said first and second dataset on a computer environment, wherein said first data comprises all said services of all units of work having an active or terminated status, and said selected part of said first data comprises all the current services of all units of work having an active status.

19. A method of executing queries within a relational database comprising,
   a first set of tables comprising first columns and first tuples and a first dataset containing first data located in said first columns and first tuples; and a second set of tables comprising second columns and second tuples and a second dataset comprising of second data, all the data located in said second columns and second tuples being second data, said units of work comprising first services, final services and current services, said unit of work having a status being inactive, active or terminated, wherein said second data is a redundant representation of a part of said first data, the method comprising:

selecting tuples in said second set of tables, and reading out the tuples of said first set of tables corresponding to said selected tuples of said second tables.

20. A method of executing queries within the relational database comprising, a first set of tables comprising first columns and first tuples and a first dataset containing first data located in said first columns and first tuples, and a second set of tables comprising second columns and second tuples and a second dataset comprising second data, all the data located in said second columns and second tuples being second data, said units of work comprising first services, final services and current services, said unit of work having a status being inactive, active or terminated, wherein said second data is a redundant representation of a part of said first data, each of said data is an electronic message capable of representing contents of electronic forms, a set of messages being related as a unit of work, the method comprising:

selecting tuples of said second set of tables corresponding to said unit; and reading out the attributes corresponding to one column and one tuple of said first set of tables corresponding to said selected tuples of said second tables corresponding to said unit.

21. A database access system compiled on a computer environment, comprising:

a relational database configured to be accessible by application programs executing a query including:

a first set of tables with first columns and tuples containing first data, a second set of tables with second columns and tuples containing second data, each of said second data being a redundant representation of at least one of said first data; said database being adapted for access by application programs executing a query in said database;

a meta-data; and means for optimizing the accessing of said database, said means comprising tools for retaining a set of meta-data after said first data is inserted in said database, said meta-data verifying errors in an insertion of next first data in said database.

22. A system for developing software for an application to be compiled on a set of computers, said system comprising:

a relational database configured to be accessible by application programs executing a query comprising:

a first set of tables with first columns and tuples containing first data, said first data being electronic messages representing contents of electronic forms, and a second set of tables with second columns and tuples containing second data, each of said second data representing at least one of said first data;

first tools supporting a user interface;

second tools accessing said database; and third tools implementing said electronic messages and linking said database with said user interface to thereby store said electronic messages and linking said database with said user interface to thereby store said electronic messages as data in said database and whereby said electronic messages can be entered or accessed via said user interface.

23. The system of claim 22, further comprising means for adding, omitting and correcting said electronic messages.

24. The system of claim 23, wherein said means include a rulebase comprising first rules for checking data integrity before adding said data, second rules for executing the steps of omitting and adding data after corrected data are entered, and third rules for closing said user interface.

25. The system of claim 24, wherein said electronic messages represent essences consisting of the group of processes, operations, services, acts, objects, and persons within a defined world.

26. The system of claim 22, wherein said second tools comprise tools for entering said electronic messages in said database as tuples with columns in a specific table.

27. The system of claim 22, wherein said relational database is a Sybase type of database, said user interface is a workstation or a terminal and said tools are developed in Prolog.

28. The system of claim 22, further comprising modules being specific for one application according to one of said essences within said defined world.

29. The system of claim 22, wherein a set of the first data being comprised in said database is displayed on said user interface.

30. The system of claim 29, wherein said first tools comprise means for maintaining a subset of said set of first data on said user interface while storing said set of first data.

31. The system of claim 30, wherein said set of first data is represented as a graph with nodes representing parts of said set of first data and arcs representing the inter-relationships of said parts.

32. The system of claim 31, further comprising means for browsing said graph.

33. The system of claim 22, further comprising fourth tools for developing a specific application including means for generating database objects associated with said electronic forms.

34. A clinical workstation implementing on a computer environment a representation of a group of processes, operation, services, acts, objects and persons within a hospital comprising:

a relational database configured to be accessible by application programs executing a query comprising:

a first set of tables with first columns and tuples containing first data, said first data being electronic messages being the contents of electronic forms wherein said first set of tables is organized as a set of generalized tables according to the different types of said operations, and a second set of tables with second columns and tuples containing second data, each of said second data being a redundant representation of at least one of said first data;

software modules, integrating a medically logical unit of said hospital;

a user interface including a dashboard and integrating said modules; and a generator stored on said computer environment comprising:
first tools supporting a user interface;
second tools accessing said database; and
third tools implementing said electronic messages and linking said database with said user interface whereby said messages can be entered or accessed via said user interface.

35. The clinical workstation of claim 34, wherein said user interface includes a dashboard on a computer screen, said dashboard comprising a palette with buttons representing said objects, persons, processes, services, operations or acts within said hospital.

36. The clinical workstation of claim 34, wherein said set of generalized first tables comprise a standard, fixed and variable part.

37. The clinical workstation of claim 36, wherein said standard part is determined by the type of operation, said fixed part is determined by a specific service, and said variable part is determined by said service.

38. The clinical workstation of claim 34, further comprising units of work linked to said third tools for checking integrity of said messages.

39. A hospital information system stored on a network of computers and workstations comprising:
a relational database stored on at least one computer of said network and configured to be accessible by application programs executing a query comprising:
a first set of tables with first columns and tuples containing first data, said first data being electronic messages being the contents of electronic forms, and
a second set of tables with second columns and tuples containing second data, each of said second data representing at least one of said first data;
a generator stored on at least one computer of said network comprising:
first tools supporting a user interface;
second tools accessing said database;
third tools implementing said electronic messages and linking said database with said user interface whereby said messages are stored as data in said database and whereby said messages can be entered or accessed via said user interface; and
at least one clinical workstation comprising said user interface and modules allowing for entry of essences consisting of the group of processes, operations, services, acts and objects related to a patient's medical file within the hospital.

40. The hospital information system of claim 39, further comprising data related to a patient's administrative file within the hospital.

* * * * *